United States Patent
Kim et al.

(10) Patent No.: US 12,180,537 B2
(45) Date of Patent: Dec. 31, 2024

(54) COMPOSITION FOR DETECTING dsRNAs, COMPRISING MEROCYANINE COMPOUND AND ISOMER THEREOF, AND METHOD FOR PROVIDING INFORMATION FOR DIAGNOSING CANCER, BY USING dsRNA EXPRESSION ANALYSIS

(71) Applicant: KOREA ADVANCED INSTITUTE OF SCIENCE AND TECHNOLOGY, Daejeon (KR)

(72) Inventors: Yoosik Kim, Daejeon (KR); Raisa Kharbash, Daejeon (KR); Ahsan Ausaf Ali, Daejeon (KR); Minjeong Kang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 511 days.

(21) Appl. No.: 16/968,992

(22) PCT Filed: Apr. 19, 2019

(86) PCT No.: PCT/KR2019/004776
§ 371 (c)(1),
(2) Date: Aug. 11, 2020

(87) PCT Pub. No.: WO2020/050470
PCT Pub. Date: Mar. 12, 2020

(65) Prior Publication Data
US 2021/0024981 A1 Jan. 28, 2021

(30) Foreign Application Priority Data

Sep. 7, 2018 (KR) .................. 10-2018-0107244
Dec. 13, 2018 (KR) .................. 10-2018-0161306

(51) Int. Cl.
*C12Q 1/68* (2018.01)
*C12Q 1/6809* (2018.01)

(52) U.S. Cl.
CPC .................. *C12Q 1/6809* (2013.01)

(58) Field of Classification Search
USPC .......... 435/6.1, 6.11, 91.1; 436/94; 536/23.1
See application file for complete search history.

(56) References Cited

U.S. PATENT DOCUMENTS

2003/0118993 A1* 6/2003 Kaul ................. A61P 35/00
  435/6.16
2009/0280060 A1 11/2009 Marriott et al. ........... 424/9.1

FOREIGN PATENT DOCUMENTS

| EP | 2518144 | 10/2012 |
|---|---|---|
| EP | 3235909 | 10/2017 |
| WO | 2008109558 | 9/2008 |

OTHER PUBLICATIONS

Li et al. "Double-stranded RNA released from damaged articular chondrocytes promotes cartilage degeneration via Toll-like receptor 3-interleukin-33 pathway" Cell Death and Disease 2017 8:e3165 pp. 1-13.

(Continued)

*Primary Examiner* — Frank W Lu
(74) *Attorney, Agent, or Firm* — Licata & Tyrrell P.C.

(57) ABSTRACT

The merocyanine compound of the present invention causes a spectral change of a hypochromic shift in the vicinity of the wavelength of 512 nm by intercalation between dsRNA nucleotide pairs, and the spectral change shows high accuracy and reproducibility, so the merocyanine compound of the present invention can be effectively used for detecting dsRNA and comparing the expression levels between samples. In addition, the present invention relates to a (Continued)

composition for detecting dsRNA comprising a merocyanine compound, a salt thereof or an isomer thereof.

3 Claims, 31 Drawing Sheets

Specification includes a Sequence Listing.

(56) References Cited

OTHER PUBLICATIONS

Andersson et al. "Photoswitched DNA-Binding of a Photochromic Spiropyran", Journal of the American Chemical Society 2008 130 (36) 11836-11837.
Andersson et al. "Light controlled DNA-binding of spiropyrans", Collection Symposium Series 2008 pp. 305-306.
Ali et al. "Photoswitched interatctions of Spiropyran and dsRNA", The Korean Society for Biotechnology and Bioengineering 2018 pp. 471-472.
Ali et al. "Spiropyran as a potential molecular diagnostic tool for double-stranded RNA detection" BMC Biomedical Engineering 2019 1:6 pp. 1 to 13.
Wang et al. "dsRNA sensors and plasmacytoid dendritic cells in host defense and autoimmunity" Immunol Rev. 2011 243:74-90.
Chen et al. "The role of microRNAs in the pathogenesis of autoimmune diseases" Autoimmunity Reviews 2016 15:1171-1180.

* cited by examiner 1. ladder
2. Total RNA of HeLa cells
3. Total RNA+RNase T1 of HeLa cells
4. Total RNA+RNase A of HeLa cells

COMPOSITION FOR DETECTING dsRNAs, COMPRISING MEROCYANINE COMPOUND AND ISOMER THEREOF, AND METHOD FOR PROVIDING INFORMATION FOR DIAGNOSING CANCER, BY USING dsRNA EXPRESSION ANALYSIS

This patent application is the National Stage of International Application No. PCT/KR2019/004776 filed Apr. 19, 2019, which claims the benefit of priority from Korean Application No. 10-2018-0107244, filed Sep. 7, 2018, and Korean Application No. 10-2018-0161306 filed Dec. 13, 2018, teachings of each of which are herein incorporated by reference in their entirety.

BACKGROUND OF THE INVENTION

1. Field of the Invention

The present invention relates to a composition for detecting dsRNA and a method for providing information for the diagnosis of cancer using dsRNA.

2. Description of the Related Art

Double-stranded RNA (dsRNA), first discovered in retroviruses, has been considered as a byproduct of viral replication in mammals. The dsRNA expressed in mammalian cells is recognized by innate immune response proteins to induce interferons, inhibit protein translation and induce apoptosis. The interesting thing in the dsRNA-mediated signal transduction is that the immune response protein recognizes a specific structure of RNA, such as the secondary structure rather than the specific sequence.

Although dsRNA is closely related to immune response through the antiviral signal transduction, evidences have been reported that human cells naturally express dsRNA capable of regulating antiviral machinery in various cellular environments. RNA in the mitochondria can exist as intermolecular dsRNA, which can bind to PKR and regulate the signaling activity thereof. It has also been found that the accumulation of endogenously encoded dsRNA is associated with the development of autoimmunity and age-related macular degeneration (Wang, Y M, Swiecki, M, McCartney, S A and Colonna, M (2011) dsRNA sensors and plasmacytoid dendritic cells in host defense and autoimmunity *Immunol Rev*, 243, 74-90).

The present inventors confirmed that the merocyanine compound can be effectively used for detecting dsRNA and comparing the expression levels between samples, and that the disease related to dsRNA overexpression can be diagnosed by measuring the expression level of dsRNA, thereby completed the present invention.

SUMMARY OF THE INVENTION

It is an object of the present invention to provide a composition for detecting dsRNA comprising a merocyanine compound, a salt thereof or an isomer thereof.

It is another object of the present invention to provide a kit for detecting dsRNA comprising the composition of the present invention.

It is another object of the present invention to provide a method for detecting dsRNA using the merocyanine compound of the present invention.

It is another object of the present invention to provide a method for providing information for the diagnosis of cancer.

It is another object of the present invention to provide a method for predicting the responsiveness of a cancer patient to an anticancer agent.

It is another object of the present invention to provide a method for providing information for the diagnosis of degenerative joint disease.

It is another object of the present invention to provide a method for providing information for the diagnosis of Sjogren's syndrome.

To achieve the above objects, the present invention provides a composition for detecting dsRNA comprising a merocyanine compound represented by formula 1 below, a salt thereof or an isomer thereof:

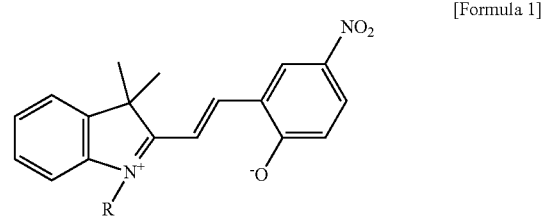

[Formula 1]

(In formula 1, R is —$CH_2CH_2CH_2N^+(CH_3)_3$).

The present invention also provides a kit for detecting dsRNA comprising the composition of the present invention.

The present invention also provides a method for detecting dsRNA comprising the following steps:

1) preparing a merocyanine compound, an isomer generated by irradiating UV to a merocyanine compound represented by formula 1 or a spiropyran compound represented by formula 2 below;
2) extracting dsRNA by treating RNase to the each RNA separated from the control and experimental group samples;
3) reacting the merocyanine compound of step 1) and the dsRNA of step 2); and
4) comparing the amount of dsRNA in the reaction solution of step 3).

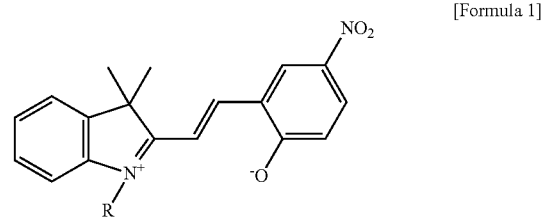

[Formula 1]

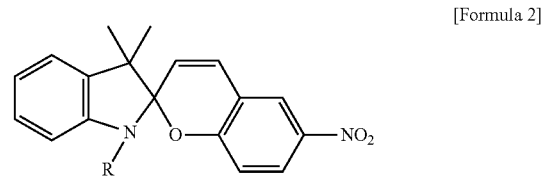

[Formula 2]

(In formula 1 and formula 2, R is —$CH_2CH_2CH_2N^+(CH_3)_3$).

The present invention also provides a method for providing information for the diagnosis of cancer comprising the following steps:

1) measuring the expression level of dsRNA in a sample of a test subject; and
2) comparing the expression level of dsRNA measured in step 1) with that of the normal control group.

The present invention also provides a method for predicting the responsiveness of a cancer patient to an anticancer agent comprising the following steps:
1) treating the cancer patient sample with an anticancer agent;
2) measuring the expression level of dsRNA in the sample treated with the anticancer agent of step 1); and
3) comparing the expression level of dsRNA measured in step 2) with that of the normal control group.

The present invention also provides a method for providing information for the diagnosis of degenerative joint disease comprising the following steps:
1) measuring the expression level of dsRNA in a sample of a test subject; and
2) comparing the expression level of dsRNA measured in step 1) with that of the normal control group.

In addition, the present invention provides a method for providing information for the diagnosis of Sjogren's syndrome comprising the following steps:
1) measuring the expression level of dsRNA in a sample of a test subject; and
2) comparing the expression level of dsRNA measured in step 1) with that of the normal control group.

ADVANTAGEOUS EFFECT

The merocyanine compound of the present invention causes a spectral change of a hypochromic shift in the vicinity of the wavelength of 512 nm by intercalation between dsRNA nucleotide pairs, and the spectral change shows high accuracy and reproducibility, so the merocyanine compound of the present invention can be effectively used for detecting dsRNA and comparing the expression levels between samples.

In addition, the present invention can provide information for the diagnosis of degenerative joint disease or Sjogren's syndrome, as well as cancer by measuring the expression level of dsRNA separated from a sample of a test subject and comparing it with that of the normal control group. Further, the responsiveness of a patient to the treated drug can be predicted by treating the sample with a drug and measuring the expression level of dsRNA.

A: poly AU 0, 175, 300, 420, 480, 620 μM;
B: poly GC 0, 90, 200, 300, 350, 650 μM;
C: poly AU 0, 90, 140, 220, 300, 350, 440 μM;
D: poly GC 0, 90, 150, 200, 350, 440 μM.

Figure 4:
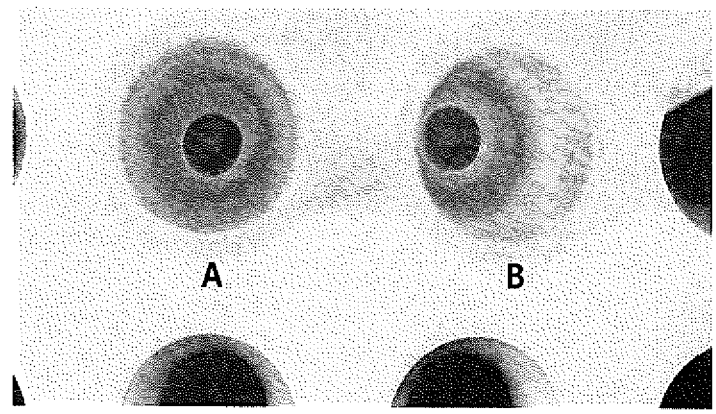

FIG. 4 is a diagram showing the color change of merocyanine induced by adding poly GC dsRNA to the merocyanine solution: A: control group (water); B: dsRNA treated group.

Figure 5A:
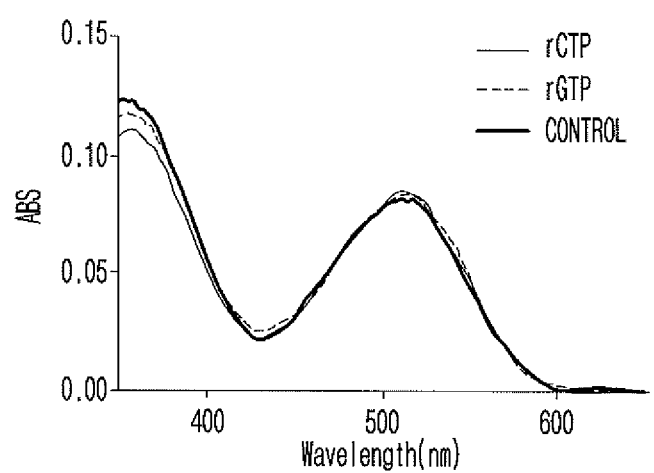
Figure 5B:
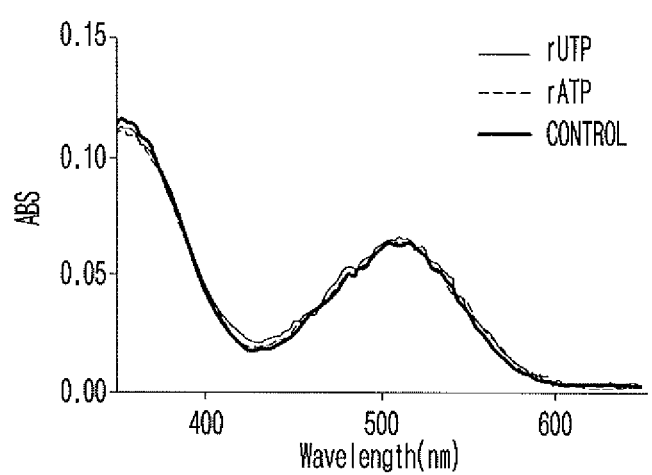

FIG. 5 is a set of graphs showing the results of measuring the absorbance after adding the RNA single nucleotides rCTP, rGTP, rUTP and rATP to the merocyanine solution, respectively: FIG. 5A: rCTP and rGTP; FIG. 5B: rUTP and rATP.

Figure 6:
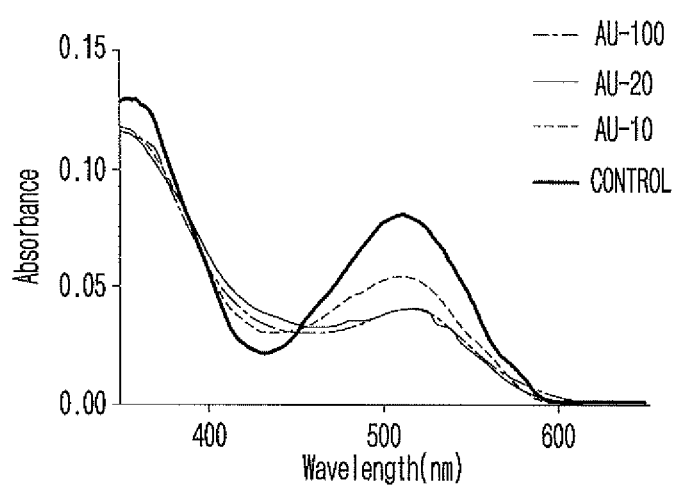

FIG. 6 is a graph showing the results of measuring the absorbance after adding 10-, 20-, and 100-mer poly AU to the merocyanine solution, respectively.

Figure 7A:
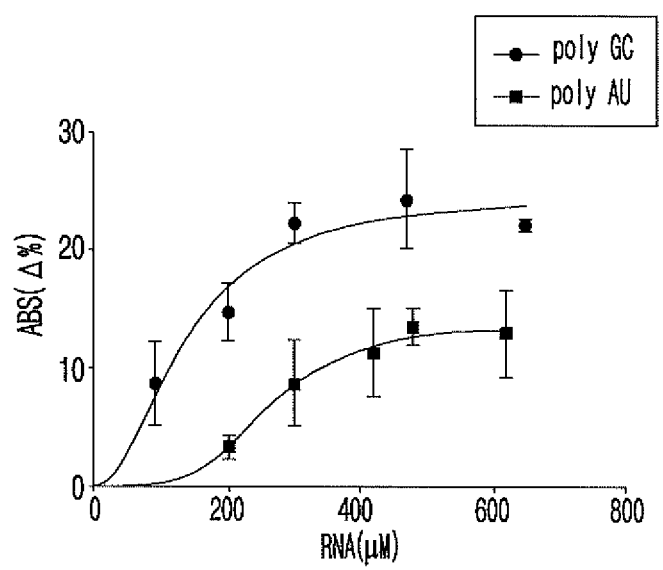
Figure 7B:
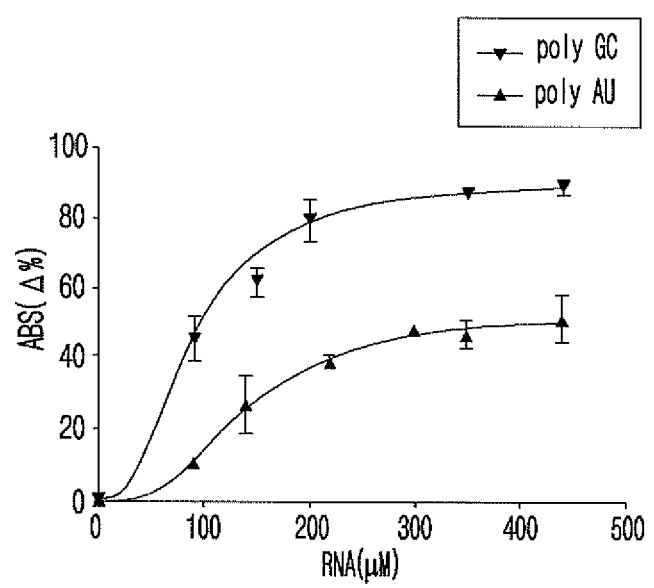

FIG. 7 is a set of graphs showing the results of quantifying the change in absorbance at 512 nm after adding poly AU and poly GC, and converting spiropyran (SP, 12 μM) to merocyanine (MC) in buffer (FIG. 7A) of pH 7 containing 9 mM sodium ion or water (FIG. 7B) of pH 7 without nuclease and sodium:

A: poly AU 0, 175, 300, 420, 480, 620 μM; poly GC 0, 90, 200, 300, 350, 650 M;
B: poly AU 0, 90, 140, 220, 300, 350, 440 μM; poly GC 0, 90, 150, 200, 350, 440 μM.

Figure 8:
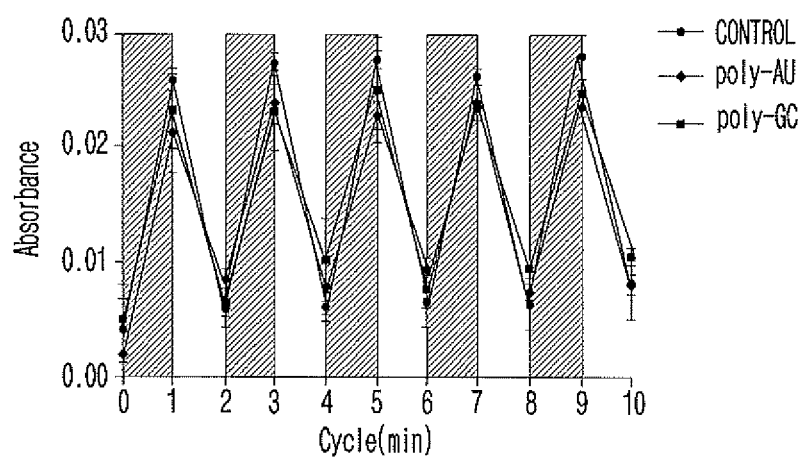

FIG. 8 is a graph showing the results of measuring the absorbance when poly AU and poly GC were added to the spiropyran solution and UV and visible light were irradiated thereto alternately: grey area: UV irradiated; white area: visible light irradiated.

Figure 9:

FIG. 9 is a diagram showing the results of electrophoresis after treating RNase T1 and RNase A to the total RNA extracted from HeLa cervical cancer cells.

Figure 10:
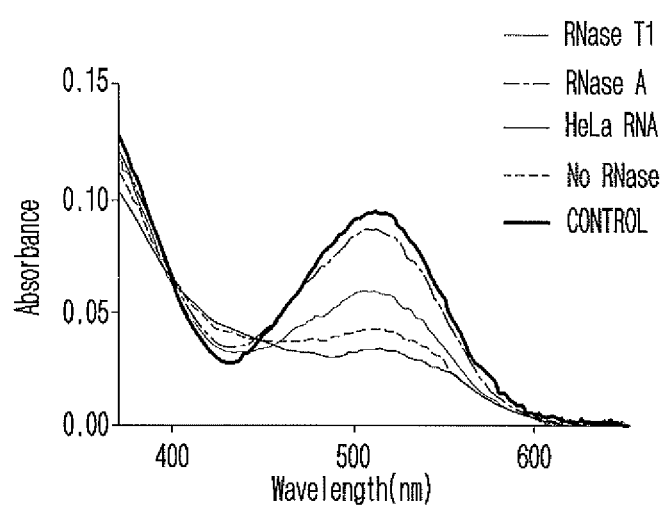

FIG. 10 is a graph showing the results of measuring the absorbance at 512 nm after treating RNase T1 and RNase A to the total RNA extracted from HeLa cervical cancer cells:
Control: water;
RNase A: HeLa RNA+RNase A treated;
RNase T1: HeLa RNA+RNase T1 treated;
No RNase: HeLa RNA (stored at room temperature for 30 minutes)+RNase non-treated;
HeLa RNA: HeLa RNA+RNase non-treated.

Figure 11:
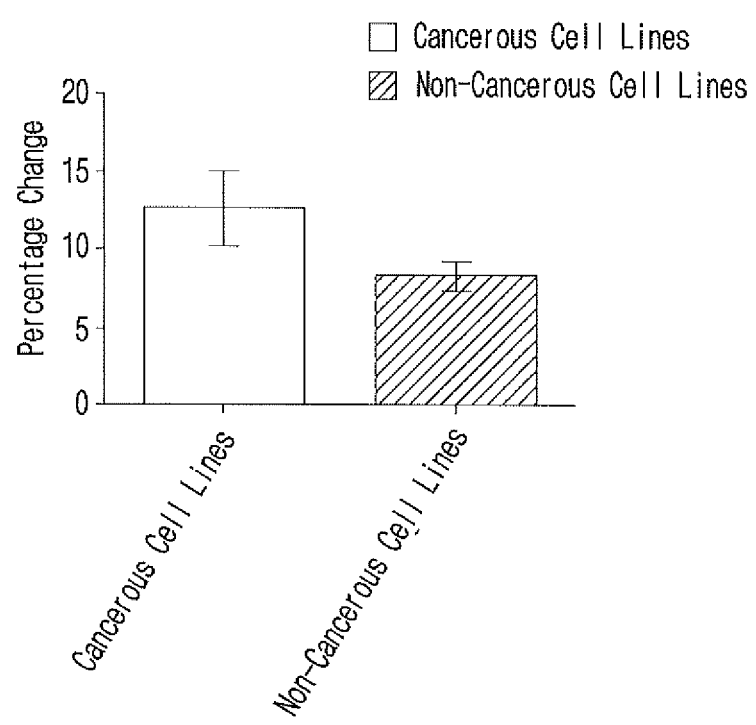

FIG. 11 is a graph showing the average rate of changes in absorbance at 512 nm in cancer cells and normal cells when UV was irradiated after mixing spiropyran and dsRNA extracted from cancer cells (HeLa cervical cancer cells, HCT116 colorectal cancer cells and A549 lung cancer cells) and normal cells (CCD-986sk cells and RPE-1 cells), respectively.

Figure 12:
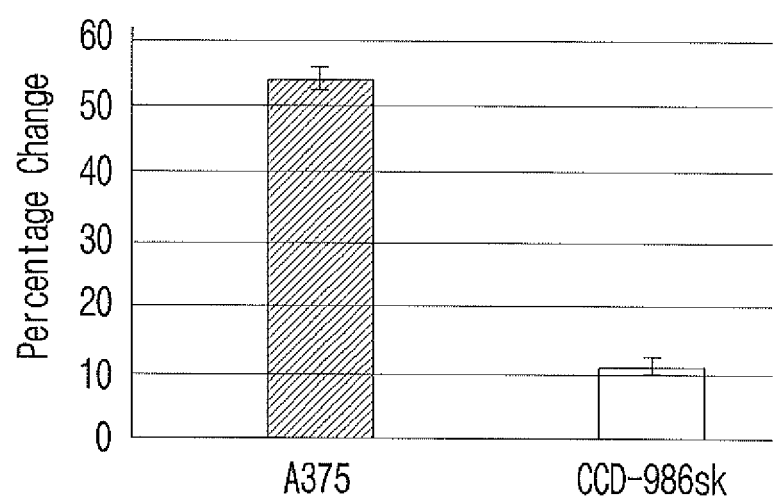

FIG. 12 is a graph showing the average rate of changes in absorbance at 512 nm (n=3) in cells when UV was irradiated after mixing spiropyran and dsRNA extracted from A375 (skin cancer melanoma cells) and CCD-986sk (normal primary skin fibroblast).

Figure 13A:
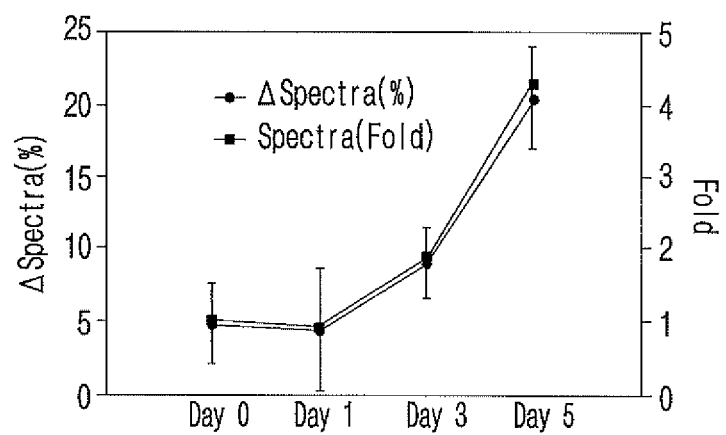
Figure 13B:
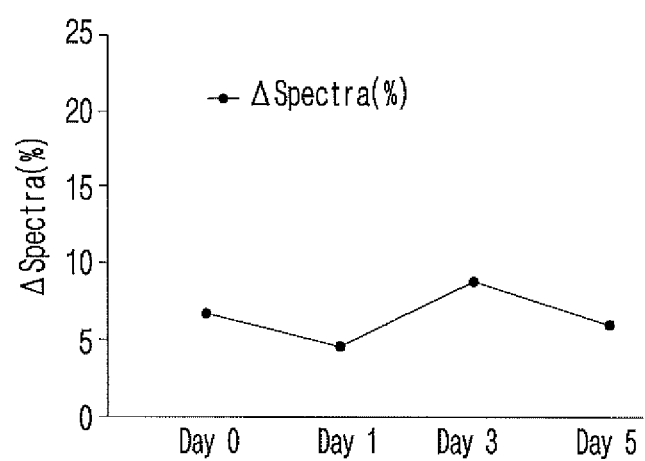
Figure 14A:
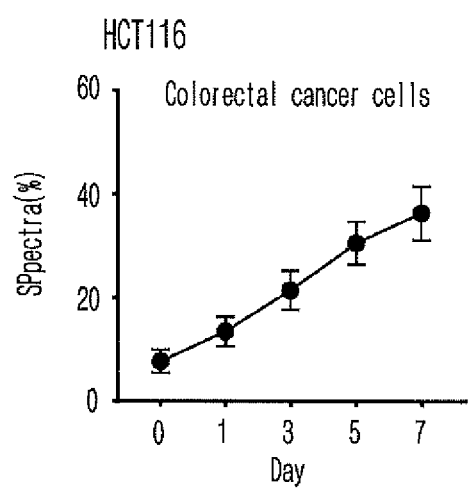
Figure 14B:
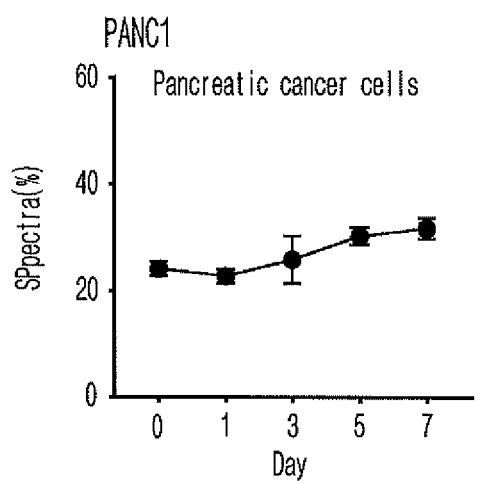
Figure 14C:
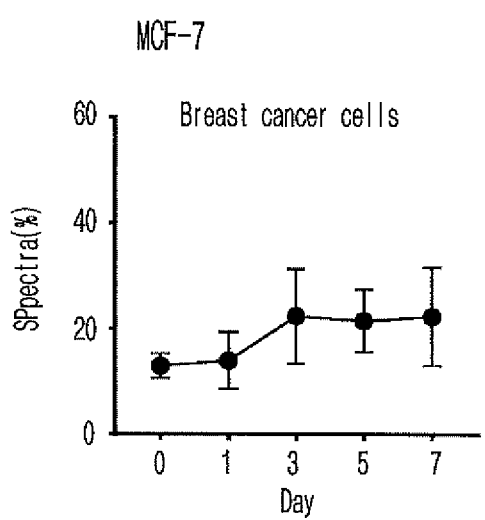
Figure 14D:
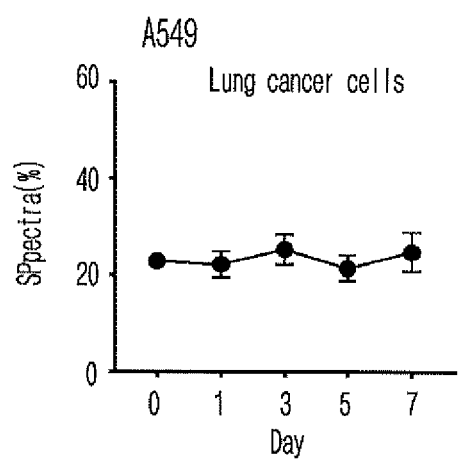
Figure 14E:
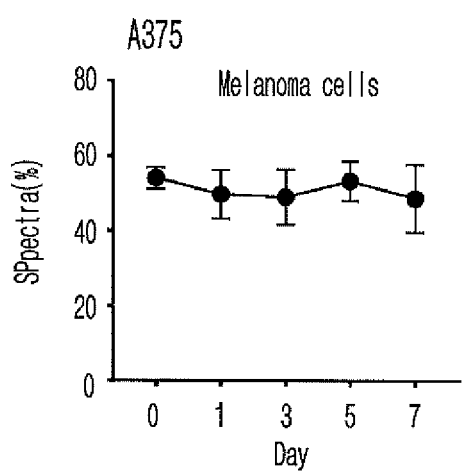

FIG. 13 is a set of graphs showing the rate of change in absorbance when UV was irradiated after mixing spiropyran and dsRNA extracted from HCT116 colorectal cancer cells (FIG. 13A) and HeLa cervical cancer cells (FIG. 13B) treated with 5-AZA-CdR, respectively.

FIG. 14 is a set of graphs showing the rate of change in absorbance when UV was irradiated after mixing spiropyran and dsRNA extracted from HCT116 colorectal cancer cells (FIG. 14A), PANC1 pancreatic cancer cells (FIG. 14B), MCF-7 breast cancer cells (FIG. 14C), A549 lung cancer cells (FIG. 14D), and A375 melanoma cells (FIG. 14E) treated with 5-AZA-CdR, respectively.

Figure 15A:
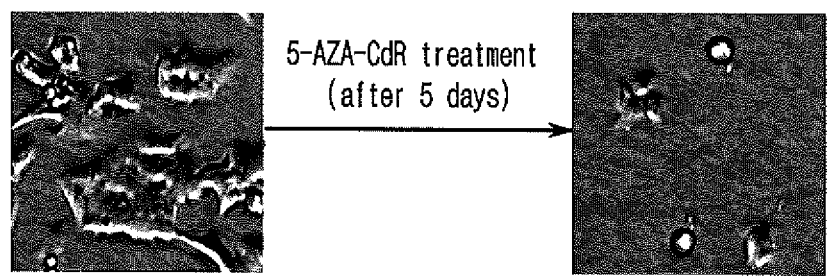
Figure 15B:
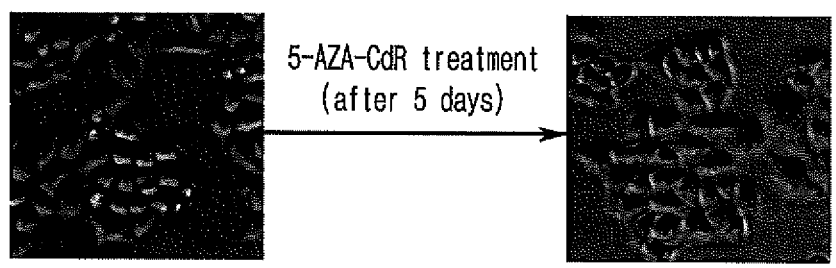

FIG. 15 is a set of photographs of HCT116 colorectal cancer cells (FIG. 15A) and HeLa cervical cancer cells (FIG. 15B) taken before and 5 days after the treatment of 5-AZA-CdR.

Figure 16:
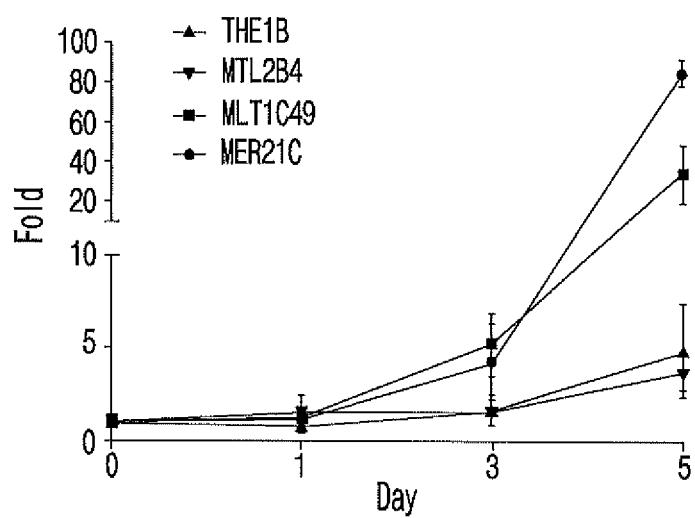

FIG. 16 is a graph showing the results of measuring the expression of ERV (THE1B, MTL2B4, MLT1C49 and MER21C) in HCT116 colorectal cancer cells induced by the treatment of 5-AZA-CdR using RT-PCR.

Figure 17:
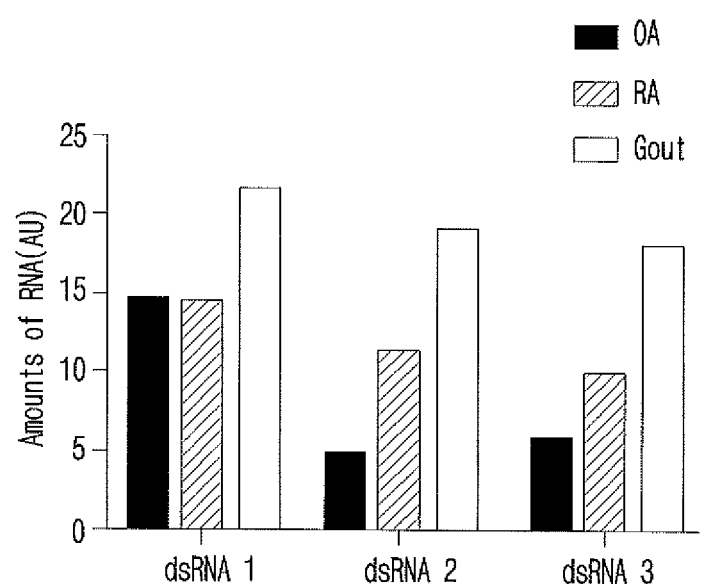

FIG. 17 is a graph showing the results of measuring the expression of 12 s dsRNA (dsRNA 1), ND1 mt dsRNA (dsRNA 2) and ND5 mt dsRNA (dsRNA 3) present in the synovial fluid obtained from patients with degenerative joint disease using RT-PCR.

Figure 18:
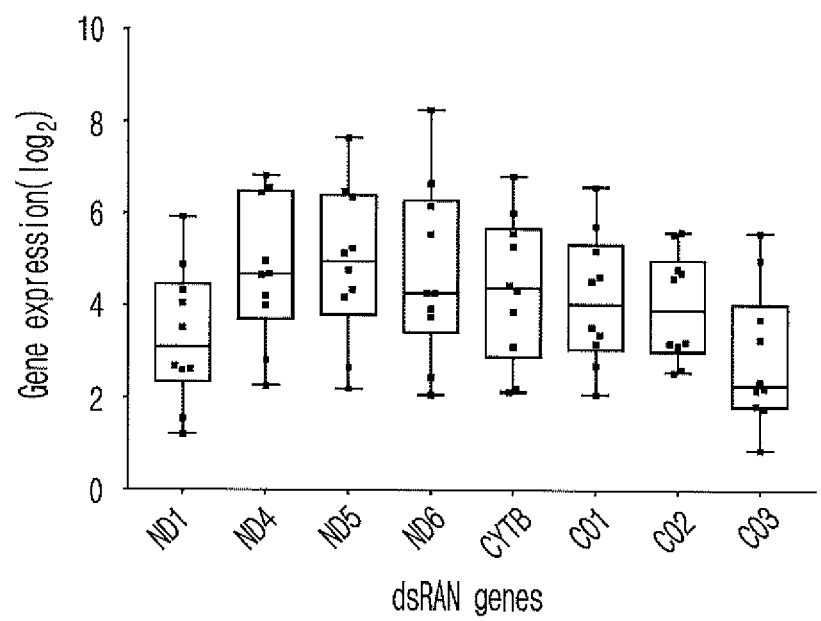

FIG. 18 is a graph showing the results of measuring the expression of ND1 dsRNA, ND4 dsRNA, ND5 dsRNA, ND6 dsRNA, CYTB dsRNA, CO1 dsRNA, CO2 dsRNA and CO3 dsRNA present in the synovial fluid obtained from 10 RA-osteoarthritis patients (OA) using RT-PCR.

Figure 19:
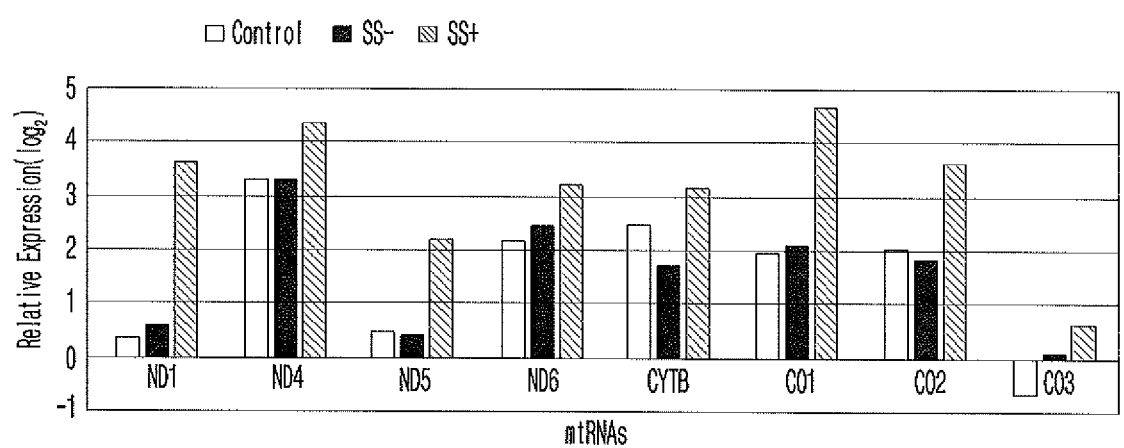

FIG. 19 is a graph showing the results of measuring the expression of ND1 dsRNA, ND4 dsRNA, ND5 dsRNA, ND6 dsRNA, CYTB dsRNA, CO1 dsRNA, CO2 dsRNA and CO3 dsRNA present in the saliva obtained from the samples of 12 normal control people (control), 12 simple xerostomia patients (SS−) and 12 Sjogren's syndrome (SS+) patients with xerostomia using RT-PCR.

DESCRIPTION OF THE PREFERRED EMBODIMENTS

Hereinafter, the present invention is described in detail.

The present invention provides a composition for detecting dsRNA comprising a merocyanine compound represented by formula 1 below, a salt thereof or an isomer thereof:

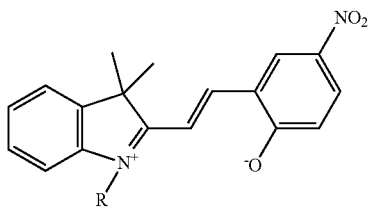

[Formula 1]

(In formula 1, R is —$CH_2CH_2CH_2N^+(CH_3)_3$).

The merocyanine compound can be an isomer produced by irradiating UV to a spiropyran compound represented by formula 2 below:

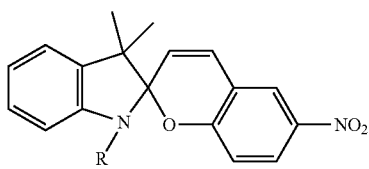

[Formula 2]

(In formula 2, R is —$CH_2CH_2CH_2N^+(CH_3)_3$).

When the spiropyran compound is exposed to ultraviolet light, the carbon-oxygen bond inside is decomposed and the three-dimensional structure is changed to be isomerized to the merocyanine compound. Since the isomerization between the spiropyran and the merocyanine is reversible, when the visible light is irradiated to the merocyanine compound, it can be isomerized again to the spiropyran compound.

The merocyanine compound can be intercalated between dsRNA nucleotides. As the merocyanine compound is intercalated between dsRNA nucleotides, the merocyanine compound is protonated and can cause changes in UV-Vis absorbance spectrum. Particularly, as the merocyanine compound is intercalated between dsRNA nucleotides, spectral changes of hypochromic shift can appear at the wavelength of 512 nm.

The present invention also provides a kit for detecting dsRNA comprising the composition of the present invention.

The kit can additionally include an UV-Vis spectrometer. In addition, the kit can additionally include a single strand RNA degradation enzyme, a solvent (buffer), and other reagents.

The solvent can be phosphate buffer, carbonate buffer, or cacodylate buffer. Also, the solvent may or may not contain ions. Specifically, the solvent may not contain ions.

The single strand RNA degradation enzyme can be RNase T1 or RNase I, specifically, RNase T1, but not always limited thereto.

In a preferred embodiment of the present invention, the present inventors irradiated UV to the synthesized spiropyran to produce merocyanine, an isomer of spiropyran. As a result, it was confirmed that spiropyran was not combined with dsRNA, so no change was observed in the UV-Vis absorbance spectrum, whereas merocyanine was intercalated with dsRNA to change the absorbance spectrum of merocyanine (see FIGS. 1~3).

It was also confirmed that merocyanine interacted more strongly with poly GC than poly AU, and more strongly with dsRNA in a solution without ions than a solution with ions (see FIG. 3).

It was confirmed that the red merocyanine was changed to colorless merocyanine as the dsRNA of poly GC was intercalated with merocyanine (see FIG. 4).

It was confirmed that merocyanine did not bind to single nucleotide nucleic acid and was effective in detecting dsRNA of 20 bp or more (see FIGS. 5 and 6).

It was also confirmed that the higher the concentration of dsRNA, the higher the rate of change in absorbance of merocyanine. And it was confirmed that the amount of dsRNA between samples could be compared by quantifying the change in absorbance of merocyanine (see FIG. 7).

It was also confirmed that merocyanine was intercalated not only with synthetic dsRNA, but also with dsRNA extracted from real cells (see FIG. 10).

The merocyanine compound of the present invention causes a spectral change of a hypochromic shift in the vicinity of the wavelength of 512 nm by intercalation between dsRNA nucleotide pairs. And the amount of dsRNA between samples can be compared by quantifying the change in absorbance of merocyanine. The spectral change shows high accuracy and reproducibility, so the merocyanine compound of the present invention can be effectively used for detecting dsRNA and comparing the expression levels between samples.

The present invention also provides a method for detecting dsRNA comprising the following steps:

1) preparing a merocyanine compound, an isomer generated by irradiating UV to a merocyanine compound represented by formula 1 or a spiropyran compound represented by formula 2 below;

2) extracting dsRNA by treating RNase to the each RNA separated from the control and experimental group samples;
3) reacting the merocyanine compound of step 1) and the dsRNA of step 2); and
4) comparing the amount of dsRNA in the reaction solution of step 3):

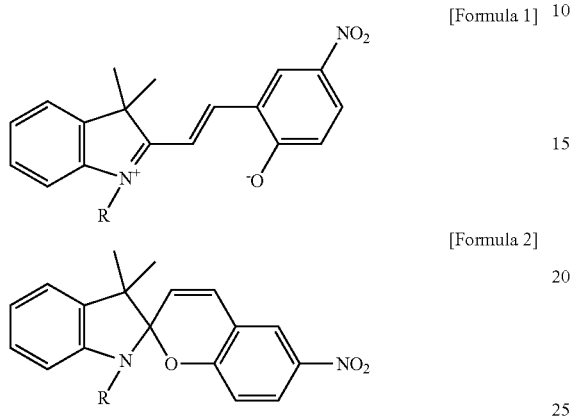

[Formula 1]

[Formula 2]

(In formula 1 and formula 2, R is —$CH_2CH_2CH_2N^+(CH_3)_3$).

In the above method, the RNase of step 2) can be RNase T1, but not always limited thereto, and an enzyme capable of degrading single strand RNA can be used without limitation. The RNase T1 can degrade single strand RNA (ssRNA) and hairpin loops.

The reaction of step 3) can be performed in a solution with or without ions. Specifically, the reaction of step 3) can be performed in a solution without ions, and the merocyanine compound exhibits a positive charge, so that the ions in the solution can interrupt the intercalation of the merocyanine compound with dsRNA.

The amount of dsRNA in step 4) can be measured by UV-Vis spectroscopy, and specifically, the amount of dsRNA in step 4) can be measured by the change in absorbance at the wavelength of 512 nm. As the merocyanine compound is intercalated between dsRNA nucleotides, the merocyanine compound is protonated and can cause changes in the UV-Vis absorbance spectrum. Particularly, as the merocyanine compound is intercalated between dsRNA nucleotides, spectral changes of hypochromic shift can occur at the wavelength of 512 nm.

The present invention also provides a method for providing information for the diagnosis of cancer comprising the following steps:
1) measuring the expression level of dsRNA in a sample of a test subject; and
2) comparing the expression level of dsRNA measured in step 1) with that of the normal control group.

The sample of step 1) can be any one selected from the group consisting of blood, serum, plasma, body fluid, saliva, urine, cells and tissues, but not always limited thereto.

The measurement of the expression level of dsRNA in step 1) can be performed by RT-PCR or UV-Vis spectroscopy, but not always limited thereto. Particularly, the expression level of dsRNA can be measured by extracting total RNA from a sample of a test subject, synthesizing cDNA, and then performing RT-PCR with a primer capable of amplifying dsRNA. Or, the measurement can be performed by extracting total RNA from a sample of a test subject, and measuring the absorbance changes that appear in response to the merocyanine compound. Specifically, the measurement of the expression level of dsRNA in step 1) can include the following steps:
i) preparing a merocyanine compound, an isomer produced by irradiating UV to the merocyanine compound represented by formula 1 or the spiropyran compound represented by formula 2;

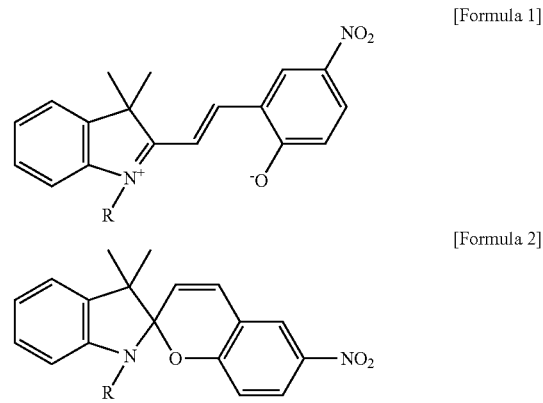

[Formula 1]

[Formula 2]

(In formula 1 and formula 2, R is —$CH_2CH_2CH_2N^+(CH_3)_3$).

ii) extracting dsRNA by treating RNase to each total RNA extracted from a test subject;
iii) reacting the merocyanine compound of step i) and the dsRNA of step ii); and
iv) measuring the absorbance of the reaction solution of step iii).

The RNase of step ii) can be RNase T1, but not always limited thereto, and an enzyme capable of degrading ssRNA can be used without limitation. The said RNase T1 can degrade ssRNA and hairpin loops. The reaction of step iii) can be performed in a solution with or without ions. Specifically, the reaction of step iii) can be performed in a solution without ions, and the merocyanine compound exhibits a positive charge, so that the ions in the solution can interrupt the intercalation of the merocyanine compound with dsRNA.

The absorbance of step iv) can be measured at the wavelength of 512 nm.

In addition, the measurement of the expression of dsRNA can further include a step of calculating the rate of change in absorbance by comparing the absorbance of step iv) with that of the reaction solution without dsRNA. Cancer cells and normal cells can be distinguished according to the calculated rate of change in absorbance. According to an embodiment of the present invention, the expression level of dsRNA in cancer cells can be higher than the expression level of dsRNA in normal cells.

In a preferred embodiment of the present invention, the present inventors treated the merocyanine compound to each dsRNA extracted from normal cells and cancer cells, and measured the rate of change in absorbance at 512 nm. As a result, the rate of change in dsRNA absorbance in cancer cells was higher than that in normal cells, which confirmed that the expression level of dsRNA in cancer cells was higher than that in normal cells (see FIG. 11).

In a preferred embodiment of the present invention, the present inventors treated the merocyanine compound to each dsRNA extracted from A375 (skin cancer melanoma cells)

and CCD-986sk (normal primary skin fibroblast), and measured the rate of change in absorbance at 512 nm. As a result, the average rate of change in absorbance in melanoma cells was higher than that in normal cells, which confirmed that the average rate of change in absorbance in melanoma cells was higher than that in normal cells (see FIG. 12).

Therefore, the present invention can provide information for the diagnosis of cancer by distinguishing cancer cells from normal cells measuring the expression level of dsRNA extracted from a sample of a test subject.

The present invention also provides a method for predicting the responsiveness of a cancer patient to an anticancer agent comprising the following steps:
1) treating the cancer patient sample with an anticancer agent;
2) measuring the expression level of dsRNA in the sample treated with the anticancer agent of step 1); and
3) comparing the expression level of dsRNA measured in step 2) with that of the normal control group.

The sample of step 1) can be any one selected from the group consisting of blood, serum, plasma, body fluid, saliva, urine, cells and tissues, but not always limited thereto.

The measurement of the expression level of dsRNA in step 1) can be performed by RT-PCR or UV-Vis spectroscopy, but not always limited thereto. Particularly, the expression level of dsRNA can be measured by extracting total RNA from a sample of a test subject, synthesizing cDNA, and then performing RT-PCR with a primer capable of amplifying dsRNA. Or, the measurement can be performed by extracting total RNA from a sample of a test subject, and measuring the absorbance changes that appear in response to the merocyanine compound.

Specifically, the measurement of the expression level of dsRNA in step 1) can include the following steps:
i) preparing a merocyanine compound, an isomer produced by irradiating UV to the merocyanine compound represented by formula 1 or the spiropyran compound represented by formula 2;

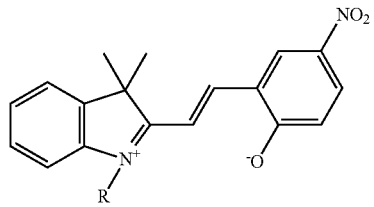
[Formula 1]

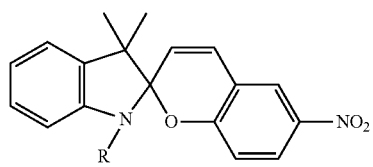
[Formula 2]

(In formula 1 and formula 2, R is —CH$_2$CH$_2$CH$_2$N$^+$(CH$_3$)$_3$).

ii) extracting dsRNA by treating RNase to each total RNA extracted from a test subject;
iii) reacting the merocyanine compound of step i) and the dsRNA of step ii); and
iv) measuring the absorbance of the reaction solution of step iii).

The RNase of step ii) can be RNase T1, but not always limited thereto, and an enzyme capable of degrading ssRNA can be used without limitation. The said RNase T1 can degrade ssRNA and hairpin loops.

The reaction of step iii) can be performed in a solution with or without ions. Specifically, the reaction of step iii) can be performed in a solution without ions, and the merocyanine compound exhibits a positive charge, so that the ions in the solution can interrupt the intercalation of the merocyanine compound with dsRNA.

The absorbance of step iv) can be measured at the wavelength of 512 nm.

In addition, the measurement of the expression of dsRNA can further include a step of calculating the rate of change in absorbance by comparing the absorbance of step iv) with that of the reaction solution without dsRNA. The reactivity to the anticancer agent can be predicted according to the calculated rate of change in absorbance. According to an embodiment of the present invention, the expression level of dsRNA in cancer cells that are highly responsive to the anticancer agent can be higher than the expression level of dsRNA in cancer cells that are not responsive to the anticancer agent.

In a preferred embodiment of the present invention, the inventors treated 5-AZA-CdR (5-aza-2'-deoxycytidine, Decitabine), a DNA demethylating agent, to HeLa cervical cancer cells known to not respond to 5-AZA-CdR and HCT116 colorectal cancer cells known to respond to 5-AZA-CdR, separated dsRNA, added the merocyanine compound thereto, and measured the rate of change in absorbance at 512 nm. As a result, the rate of change in absorbance was almost unchanged in HeLa cervical cancer cells, whereas the rate of change in absorbance was increased from day 3 of the 5-AZA-CdR treatment in HCT116 cells (see FIG. 13).

The present inventors measured the rate of change in absorbance at 512 nm after adding the merocyanine compound and dsRNA extracted from HCT116 colorectal pancreatic cancer cells, MCF-7 cancer cells, PANC1 breast cancer cells, A549 lung cancer cells, and A375 melanoma cells. As a result, it was confirmed that the rate of change in absorbance was increased from day 3 of the 5-AZA-CdR treatment in HCT116 cells. It was also confirmed that the expression of dsRNA was slightly increased on day 7 of the treatment in PANC-1 pancreatic cancer cells and MCF-7 breast cancer cells compared to day 0. In addition, it was confirmed that there was no change in the expression of dsRNA in A375 melanoma cells almost not killed by 5-AZA-CdR and A549 lung cancer cells (see FIG. 14).

The present inventors treated HeLa cervical cancer cells and HCT116 colon cancer cells with 5-AZA-CdR, respectively, and observed apoptosis of each cell. As a result, it was confirmed that apoptosis was not observed in HeLa cervical cancer cells, whereas apoptosis was observed in HCT116 cells (see FIG. 15).

The present inventors measured the expression level of ERV in cells treated with 5-AZA-CdR by qPCR, according to the report that 5-AZA-CdR treatment increased ERV (endogenous retroviral element) known to promote apoptosis. As a result, it was confirmed through qPCR that the expression of the ERV THE1B, MTL2B4, MLT1C49 and MER21C genes was increased (see FIG. 16).

Therefore, it was confirmed that the reactivity of cancer cells to an anticancer agent can be predicted by measuring the expression level of dsRNA.

The present invention also provides a method for providing information for the diagnosis of degenerative joint disease comprising the following steps:

1) measuring the expression level of dsRNA in a sample of a test subject; and 2) comparing the expression level of dsRNA measured in step 1) with that of the normal control group.

Step 1) is as described above. For example, the sample of step 1) can be any one selected from the group consisting of blood, serum, plasma, body fluid, saliva, urine, cells and tissues, but not always limited thereto. In a preferred embodiment of the present invention, the sample can be synovial fluid of a test subject.

The measurement of the expression level of dsRNA in step 1) can be performed by RT-PCR or UV-Vis spectroscopy, but not always limited thereto. Particularly, the expression level of dsRNA can be measured by extracting total RNA from a sample of a test subject, synthesizing cDNA, and then performing RT-PCR with a primer capable of amplifying dsRNA. Or, the measurement can be performed by extracting total RNA from a sample of a test subject, and measuring the absorbance changes that appear in response to the merocyanine compound.

In addition, the present invention provides a method for providing information for the diagnosis of Sjogren's syndrome comprising the following steps:

1) measuring the expression level of dsRNA in a sample of a test subject; and 2) comparing the expression level of dsRNA measured in step 1) with that of the normal control group.

Step 1) is as described above. For example, the sample of step 1) can be any one selected from the group consisting of blood, serum, plasma, body fluid, saliva, urine, cells and tissues, but not always limited thereto. In a preferred embodiment of the present invention, the sample can be saliva of a test subject.

The measurement of the expression level of dsRNA in step 1) can be performed by RT-PCR or UV-Vis spectroscopy, but not always limited thereto. Particularly, the expression level of dsRNA can be measured by extracting total RNA from a sample of a test subject, synthesizing cDNA, and then performing RT-PCR with a primer capable of amplifying dsRNA. Or, the measurement can be performed by extracting total RNA from a sample of a test subject, and measuring the absorbance changes that appear in response to the merocyanine compound.

In a preferred embodiment of the present invention, the inventors confirmed that the expression level of dsRNA in a sample isolated from a patient with degenerative joint disease was high (see FIG. 17).

The present inventors also confirmed that the expression level of dsRNA in a sample isolated from 10 patients with RA-osteoarthritis (OA) disease was high (see FIG. 18).

In addition, the present inventors confirmed that the expression level of dsRNA in a sample isolated from a patient with Sjogren's syndrome was higher than that of the normal control group (see FIG. 19).

Therefore, it was confirmed that degenerative joint disease or Sjogren's syndrome can be diagnosed by analyzing the expression level of dsRNA.

Hereinafter, the present invention will be described in detail by the following examples.

<Example 1> Preparation of Spiropyran (SP)

Step 1: Preparation of 1-(3-iodopropyl)-2,3,3-trimethylindolinium iodide (I1)

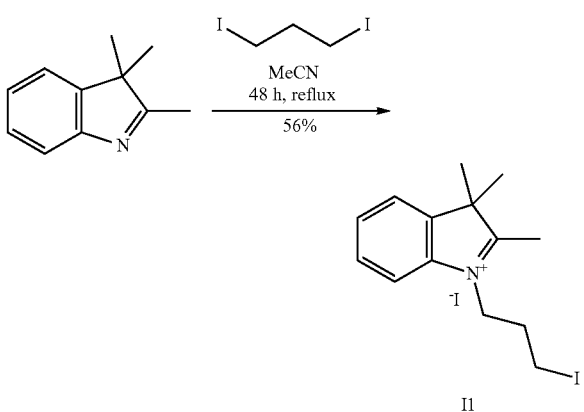

1 g (0.0062 mol) of 2,3,3-trimethylindolenine and 6.5 g (0.0219 mol) of 1,3-diiodopropane were dissolved in 2 mL of anhydrous acetonitrile, which was refluxed for 48 hours. The mixture was cooled to room temperature, and the precipitate was filtered, washed with MeCN and $CHCl_3$ and dried. As a result, 1.5 g of a grayish yellow solid was obtained (yield: 56%).

$^1$H NMR (400 MHZ, DMSO-$d_6$) δ 8.01-7.97 (1H, m), 7.88-7.83 (1H, m), 7.68-7.61 (2H, m), 4.52-4.47 (2H, t), 3.46-3.41 (2H, t), 2.87 (3H, s), 2.46-2.36 (2H, m), 1.56 (6H, s).

Step 2: Preparation of 1-(3-iodopropyl)-3,3-dimethyl-2-methyleneindoline (I2)

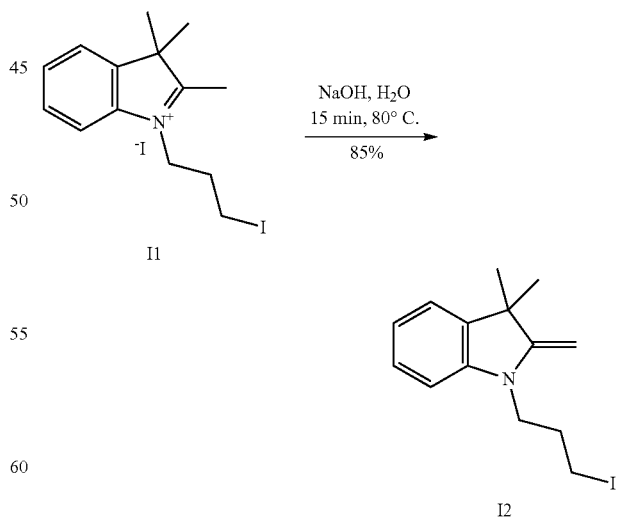

Under nitrogen atmosphere, 0.5 g (0.001 mol) of the 1-(3-iodopropyl)-2,3,3-trimethylindolinium iodide prepared in step 1 was suspended in 120 mL of degassed water, to which 1.2 g (0.03 mol) of finely ground NaOH was added.

The reaction solution was heated at 80° C. for 15 minutes, and then cooled at room temperature, to which 130 mL of ethyl ether was added. The mixture was stirred for another hour, and the aqueous layer was separated and washed with 40 mL of ethyl ether and 40 mL of dichloromethane. The organic layer was mixed, washed with water, dried over $MgSO_4$ and concentrated in vacuo. As a result, 0.30 g of a pink solid was obtained (yield: 85%).

$^1$H NMR (400 MHZ, $CDCl_3$) δ 7.09-7.04 (2H, t), 6.72-6.67 (1H, t), 6.47-6.44 (1H, d), 3.48-3.44 (2H, m), 2.22-2.15 (2H, m), 1.98-1.90 (2H, m), 1.37-1.33 (2H, d), 1.31 (6H, s).

Step 3: Preparation of 1'-(3"-iodopropyl)-3',3'-dimethyl-6-nitrospiro[(2H)-1-benzopyran-2,2'-indoline] (I3)

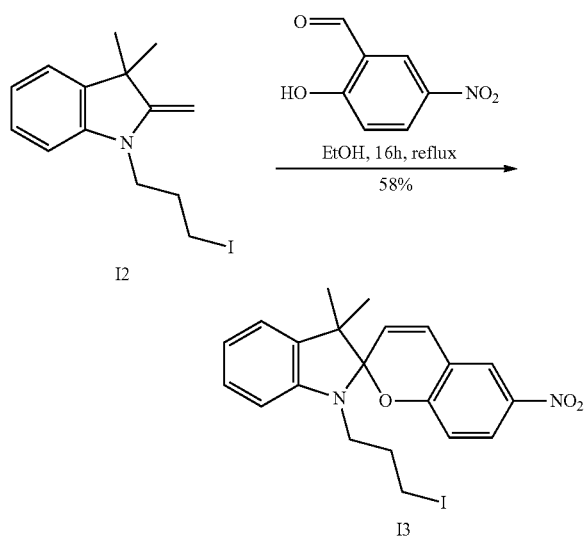

The 1-(3-iodopropyl)-3,3-dimethyl-2-methyleneindoline prepared in step 2 was dissolved in 10 mL of anhydrous ethanol, to which 0.16 g (0.0009 mol) of 5-nitrosalicylaldehyde was added. The reaction solution was refluxed under nitrogen for 16 hours. The solvent was removed in vacuo, and the residue was purified by silica gel column chromatography using hexane/dichloromethane (1:4) as an eluent, followed by recrystallization with ethanol/chloroform. As a result, 0.25 g of a yellow solid was obtained (yield: 58%).

$^1$H NMR (400 MHZ, $CDCl_3$) δ 8.02-7.99 (2H, m), 7.21-7.17 (1H, t), 7.11-7.08 (1H, d), 6.96-6.93 (1H, d), 6.91-6.87 (1H, t), 6.75-6.72 (1H, d), 6.65-6.63 (1H, d), 5.89-5.86 (1H, d), 3.35-3.11 (4H, m), 2.28-2.17 (1H, m), 2.11-2.01 (1H, m), 1.28 (3H, s), 1.18 (3H, s).

Step 4: Preparation of 1'-(3"-trimethylammoniopropyl)-3',3'-dimethyl-6-nitrospiro[(2H)-1-benzopyran-2,2'-indoline] iodide (I4)

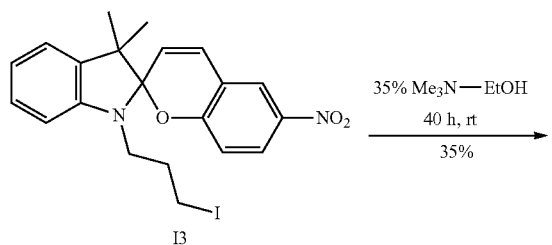

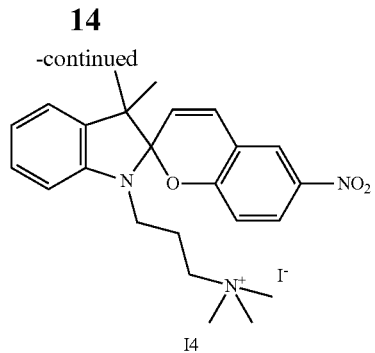

A flask containing 0.25 g (0.0005 mol) of the 1'-(3"-iodopropyl)-3',3'-dimethyl-6-nitrospiro[(2H)-1-benzopyran-2,2'-indoline] prepared in step 3 was filled with a rubber septum, to which 35% triethylamine dissolved in ethanol was added using a syringe. The reaction solution was stirred in the dark for 48 hours at room temperature. Ethanol and excess triethylamine were removed in vacuo. The residue was purified using a column, and the resulting product was suspended in ethyl ether, filtered and dried. As a result, 0.09 g of the spiropyran 1'-(3"-trimethylammoniopropyl)-3',3'-dimethyl-6-nitrospiro[(2H)-1-benzopyran-2,2'-indoline] iodide was obtained (yield: 35%).

$^1$H NMR (400 MHZ, DMSO-$d_6$) δ 8.27 (1H, s), 8.05-8.01 (1H, d), 7.27-7.24 (1H, d), 7.20-7.14 (2H, m), 6.94-6.91 (1H, d), 6.87-6.83 (1H, t), 6.76-6.73 (1H, d), 6.12-6.08 (1H, d), 3.33-3.30 (2H, m), 3.23-3.18 (2H, m), 3.03 (9H, s), 2.08-1.92 (2H, m), 1.23 (3H, s), 1.15 (3H, s).

<Example 6> Preparation of Merocyanine (MC)

The spiropyran 1'-(3"-trimethylammoniopropyl)-3',3'-dimethyl-6-nitrospiro[(2H)-1-benzopyran-2,2'-indoline] iodide prepared in Example 1 was converted into merocyanine, an isomer of spiropyran, by 254 nm UV irradiation (FIG. 10). The merocyanine can be converted back to spiropyran by visible light irradiation.

<Experimental Example 1> Binding of Spiropyran (SP) or Merocyanine (MC) and dsRNA The interaction of spiropyran (SP) or merocyanine (MC) with dsRNA was confirmed using a UV-Vis spectrometer.

<1-1> Binding of SP and dsRNA

The spiropyran produced in Example 1 was prepared as a spiropyran solution (12 μM), and dsRNA was prepared by ordering 20 bp poly GC and poly AU from Bioneer Co., Ltd., respectively. After adding 200 μM of poly GC and poly AU to the spiropyran solution, spectral results were a UV-Vis obtained using spectrometer.

Figure 1:
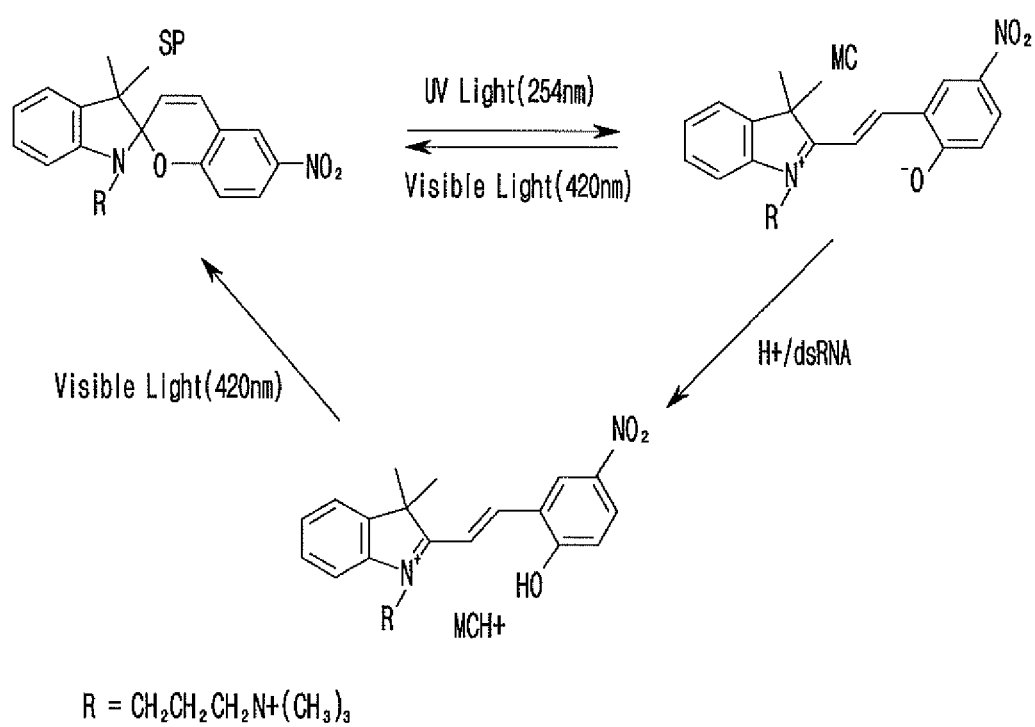
FIG. 1 is a diagram showing the structures of spiropyran (SP) that reversibly converts according to wavelengths, merocyanine (MC), an isomer of 25 light spiropyran; and protonated merocyanine ($MCH^+$) produced by combining merocyanine and dsRNA
Figure 2A:
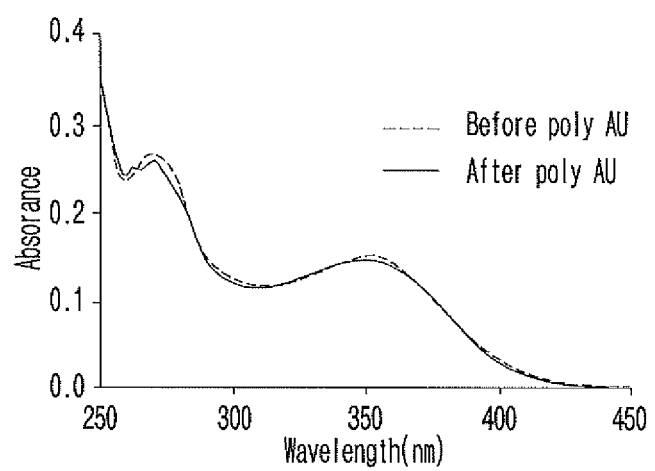
FIG. 2(A) is a set of graphs showing the results of measuring the absorbance before and after adding poly AU to the spiropyran (SP) solution, respectively.
Figure 2B:
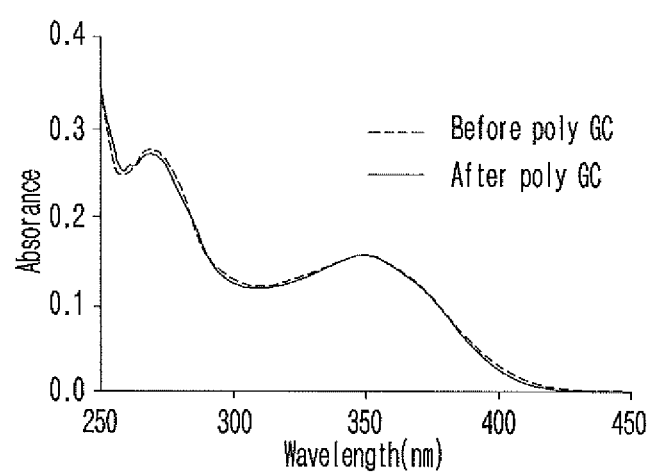
FIG. 2(B) is a set of graphs showing the results of measuring the absorbance before and after adding poly GC to the spiropyran (SP) solution, respectively.

As a result, no change in absorbance spectrum was observed in the SP solution added with poly AU and poly GC dsRNA. Therefore, it was confirmed that SP did not bind to dsRNA (FIG. 1).

<1-2> Binding of MC and dsRNA

The spiropyran produced in Example 1 was prepared as a spiropyran solution (12 μM), and dsRNA was prepared by ordering 20 bp poly GC and poly AU from Bioneer Co., Ltd., respectively. After irradiating 254 nm UV to the spiropyran solution for 5 minutes, poly GC and poly AU were added, respectively. Then, spectral results were obtained using a UV-Vis spectrometer.

Figure 3A:
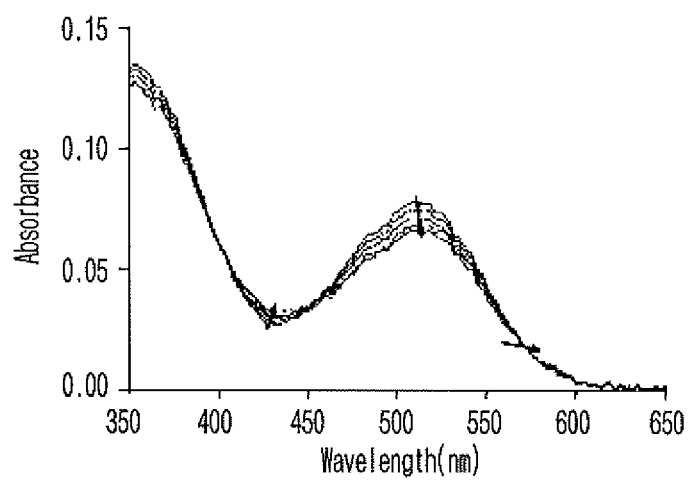
FIG. 3 is a set of graphs showing the results of measuring the absorbance after adding poly AU (A) and poly GC (B), and converting spiropyran (SP, 12 μM) to merocyanine (MC) in buffer (FIG. 3A and FIG. 3B) of pH 7 containing 9 mM sodium ion or water (FIG. 3C and FIG. 3D) of pH 7 without nuclease and sodium.
Figure 3B:
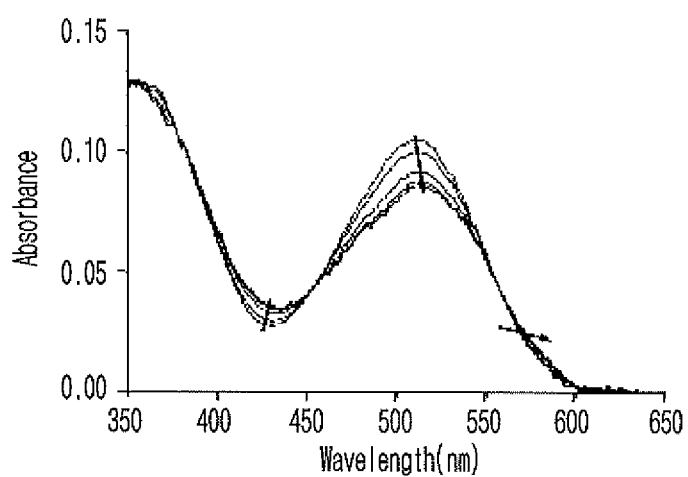
Figure 3C:
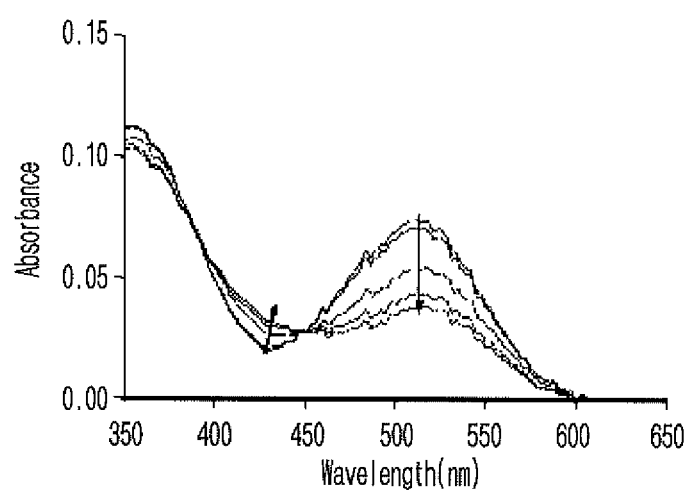
Figure 3D:
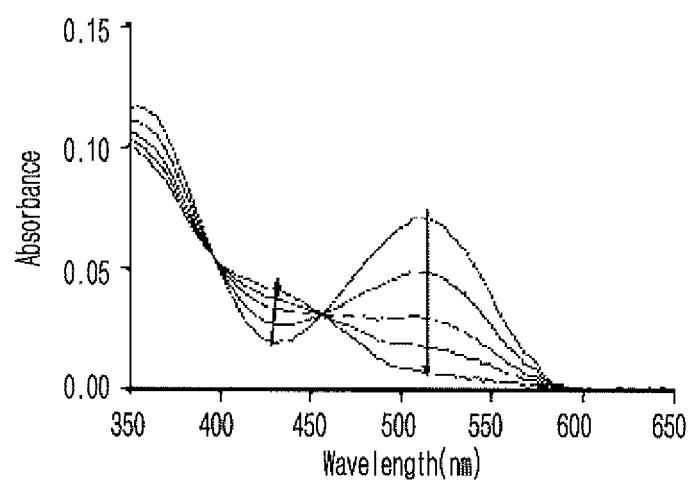

The SP exposed to UV was converted to merocyanine (MC), an open form isomer of SP (FIG. 10). The significant change in absorbance spectrum was observed in the MC solution added with poly AU and poly GC dsRNA, respectively (FIGS. 3A and 3B). A hypochromic shift and a red shift were observed at the wavelength of 512 nm, and a small but constant increase in absorbance was observed at the wavelength of 432 nm. This explains that MC is converted to protonated MC (MCH+) by intercalation between nucleotide pairs of dsRNA. In addition, when poly GC was added rather than poly AU, the changes in the spectrum such as a pale shift and a red shift appeared to be more prominent, indicating that MC has a high binding capacity to poly GC-rich RNA.

<Experimental Example 2> MC-dsRNA Binding by Ion Concentration

The effect of the ion concentration of the solution on the interaction of MC and dsRNA was investigated.

After converting 12 µM SP to MC in the same manner as described in Experimental Example <1-2> in 9 mM sodium ion (Na+) buffer (pH 7) or nuclease-free water without sodium ions (pH 7), poly AU and poly GC following concentrations, and were added at the absorbance was measured (A: poly AU 0, 175, 300, 420, 480, 620 µM; B: poly GC 0, 90, 200, 300, 350, 650 µM; C: poly AU 0, 90, 140, 220, 300, 350, 440 µM; D: poly GC 0, 90, 150, 200, 350, 440 µM).

As a result, the changes in the absorbance spectra were greater in water (FIGS. 3C and 3D) without sodium ions than in sodium ion buffer (FIGS. 3A and 3B). The above results indicate that sodium ions can interfere with the electrostatic interaction of positively charged MC with dsRNA (FIGS. 3A-3D).

<Experimental Example 3> Color Change According to MC-Poly GC dsRNA Binding

As the interaction between MC and poly GC' dsRNA was strong, the spectral change was prominent. The color change of the MC solution according to the binding of MC and poly GC dsRNA was observed.

After adding 20 µl of poly GC dsRNA or 20 µl of water to the MC solution (50 µl) prepared in Experimental Example <1-2>, color change of the MC solution was observed.

As a result, the color of the MC solution was changed from red to colorless (FIG. 4) by adding poly GC dsRNA, but the color was not changed by adding the control (20 µl of water). The above results indicate that dsRNA can be detected by visually observing the color change of the MC solution (FIG. 4).

<Experimental Example 4> Binding of MC and Single Nucleotides

To confirm the interaction between MC and single nucleotides, spectrum results were obtained in the same manner as described in Experimental Example <1-2>, except that 4 types of the RNA single nucleotides rCTP, rGTP, rUTP and rATP were used instead of dsRNA in Experimental Example <1-2>. At this time, water was used instead of RNA as the control.

As a result, it was confirmed that there was no change in absorbance spectrum in the MC solution added with each single nucleotide RNA nucleic acid, so that the single nucleotide RNA nucleic acid and MC did not bind (FIGS. 5A and 5B).

<Experimental Example 5> MC-dsRNA Binding by Length of dsRNA

To confirm that the length of dsRNA affects the interaction of MC-dsRNA, spectrum results were obtained in the same manner as described in Experimental Example <1-2>, except that 10, 20 and 100-mer poly AU dsRNA were used respectively instead of using 20-mer poly AU and poly GC dsRNA in Experimental Example <1-2> and they were treated at the concentration of 350 µM per base pair. At this time, water was used instead of RNA as the control.

As a result, the MC solutions added respectively with 20-mer and 10-mer dsRNAs showed almost the same absorbance spectrum pattern, whereas the MC solution added with 10-mer dsRNA showed weak change in absorbance spectrum. Therefore, it was confirmed that MC was effective in detecting dsRNA of 20 bp or more (FIG. 6).

<Experimental Example 6> MC-dsRNA Binding by Concentration of dsRNA

To compare and quantify the UV-Vis spectral changes induced by dsRNA, the absorbance change rate observed at 512 nm according to the concentration of dsRNA was calculated.

Particularly, spectrum results were obtained in sodium ion buffer and nuclease-free water without sodium ions in the same manner as described in Experimental Examples <1-2> and 2, except that the following concentration of dsRNA was used instead of using 200 µM of dsRNA in Experimental Examples <1-2> and 2 (A: poly AU 0, 175, 300, 420, 480, 620 µM; poly GC 0, 90, 200, 300, 350, 650 µM; B: poly AU 0, 90, 140, 220, 300, 350, 440 µM; poly GC 0, 90, 150, 200, 350, 440 µM.).

As a result, the rate of change in MC absorbance was increased as the concentration of dsRNA was increased, and the rate of change in absorbance was saturated in the high RNA concentration range (FIG. 7). As shown in the previous results, the rate of change in absorbance of poly GC ds RNA was greater than that of poly AU dsRNA, and the rate of change in absorbance in nuclease-free water without sodium ions (FIG. 7B) was greater than that in sodium ion buffer (FIG. 7A). In addition, since the binding of MC-dsRNA caused a very constant change in the spectrum, it was possible to compare the amount of dsRNA between samples by quantifying the change in absorbance of MC.

<Experimental Example 7> Effect of dsRNA on Reversibility of SP and MC

The SP and MC in the isomer relationship can be converted reversibly to each other by irradiating UV or visible light. To confirm the effect of dsRNA on the reversibility of SP-MC, SP and 200 µM poly AU and poly GC were added to sodium ion buffer, respectively, and absorbance was measured by alternately irradiating the mixture with UV and 420 nm green light in 5 cycles at 1 minute intervals. At this time, water was used instead of RNA as the control.

As a result, it was confirmed that the reversibility of SP-MC was maintained independently from the presence or absence of dsRNA (FIG. 8).

<Experimental Example 8> Binding of MC and dsRNA Isolated from Cells

Whether the MC and dsRNA isolated from cells were bound was investigated. Ribosomal RNA (rRNA), which accounts for about 90% of the RNA present in the cell, has a region that forms a hairpin structure, and thus may bind weakly with MC. Therefore, after treating RNase to remove single strand RNA (ssRNA) and hairpin loops, the interaction of MC and dsRNA isolated from cells was confirmed. At this time, water was used instead of RNA as the control.

Particularly, total RNA was isolated from HeLa cervical cancer cells (TRIsure (Bioline)). The isolated total RNA was treated with RNase T1 and RNase A having different substrate specificities respectively, followed by reacting at 37° C. for 30 minutes. After confirming the degraded RNA by electrophoresis with the reaction solution treated with each RNase, spectral results were obtained in the same manner as described in Experimental Example <1-2>.

As a result, RNase T1, an RNase that breaks down ssRNA and hairpin loops, decomposed most of rRNA and fragmented thereof, leaving only long dsRNA, and RNase A decomposed all types of RNA (FIG. 9). The above results were the same in synthetic dsRNA as well as in RNA isolated from real cells. When RNase A was treated to the total RNA isolated from HeLa cervical cancer cells, the absorbance at 512 nm was almost similar to that of the control group. When dsRNA was isolated from total RNA of cells by treatment of RNase T1, the absorbance at 512 nm was decreased (FIG. 10). From the above results, it was confirmed that MC formed intercalation with the dsRNA isolated from real cells as well as synthetic dsRNA (poly AU and poly GC), thereby causing the change in absorbance spectrum.

<Experimental Example 9> Analysis of dsRNA Expression in Cancer Cells and Normal Cells <9-1> Analysis of dsRNA Expression in Cervical Cancer Cells, Colorectal Cancer Cells, Lung Cancer Cells and Normal Cells To compare the expression level of dsRNA between cancer cells and normal cells, total RNA was extracted by treating TRIsure reagents (Bioline) to 3 types of cancer cell lines (HeLa cervical cancer cells, HCT116 colorectal cancer cells and A549 lung cancer cells) and 2 types of normal cell lines (CCD-986sk cells and RPE-1 cells), respectively. The extracted total RNA (30 μg) was treated with RNase T1 (Worthington Inc.) in a volume of 1/10, and incubated at 37° C. for 30 minutes to remove ssRNA and rRNA. Then, dsRNA was purified using a phenol extraction method. The final concentration of the purified dsRNA was adjusted to 350 μM using tertiary distilled water, to which the spiropyran solution (12 μM, dissolved in tertiary distilled water) was added. After irradiating UV to the mixture, the rate of change in absorbance at 512 nm was measured for 2 minutes. The rate of change in absorbance was calculated in comparison with the control group using tertiary distilled water instead of dsRNA.

As a result, the average rate of change in absorbance in cancer cells was higher than the average rate of change in absorbance in normal cells, indicating that the expression level of dsRNA in cancer cells was higher than that in normal cells (FIG. 11).

<9-2> Analysis of dsRNA Expression in Melanoma Cells and Normal Cells

The expression levels of dsRNA in A375 skin cancer melanoma cells and normal primary skin fibroblasts were compared in the method described in Experimental Example <9-1>.

As a result, the average rate of change in absorbance in melanoma cells was higher than the average rate of change in absorbance in normal cells, indicating that the expression level of dsRNA in melanoma cells was higher than that in normal cells (FIG. 12).

<Experimental Example 10> Evaluation of Cancer Cell Responsiveness to Drug by dsRNA Expression Analysis Cancer cell responsiveness to drug was evaluated through dsRNA expression analysis using 5-AZA-CdR (5-aza-2'-deoxycytidine, Decitabine) as a DNA demethylating agent, and HeLa cervical cancer cells, HCT116 colorectal cancer cells, PANC-1 pancreatic cancer cells, MCF-7 breast cancer cells, A549 lung cancer cells and A375 melanoma cells as cancer cell lines.

<10-1> Absorbance Change Rate

HCT116 colorectal cancer cells and HeLa cervical cancer cells were treated with 5-AZA-CdR (500 nM), respectively, and cultured for 24 hours. The medium was replaced with fresh medium and the cells were collected on days 0, 1, 3 and 5 to isolate dsRNA. The rate of change in absorbance of dsRNA in cancer cells was measured in the same manner as described in Experimental Example 9.

In addition, PANC-1 pancreatic cancer cells, MCF-7 breast cancer cells, A549 lung cancer cells and A375 melanoma cells were treated with 5-AZA-CdR (500 nM), respectively, and cultured for 24 hours. The medium was replaced with fresh medium and the cells were collected on days 0, 1, 3, 5 and 7 to isolate dsRNA. The rate of change in absorbance of dsRNA in cancer cells was measured in the same manner as described in Example 1.

As a result, the rate of change in absorbance at 512 nm in HCT116 colorectal cancer cells was gradually increased with time, but, the rate of change in absorbance in HeLa cervical cancer cells at day 5 was almost similar to that of day 0 (FIG. 13). In PANC-1 pancreatic cancer cells and MCF-7 breast cancer cells, a slight increase in dsRNA expression was observed on day 7 compared to day 0, but there was little change in dsRNA expression in A549 lung cancer cells and A375 melanoma cells (FIG. 14).

<10-2> Apoptosis

HCT116 colorectal cancer cells, PANC-1 pancreatic cancer cells, MCF-7 breast cancer cells, A549 lung cancer cells and A375 melanoma cells were treated with 5-AZA-CdR in the same manner as described in Experimental Example <10-1>, and the degree of apoptosis was measured by MTT assay.

As a result, the growth of HCT116 colorectal cancer cells was reduced by about 40%, the growth of PANC-1 pancreatic cancer cells and MCF-7 breast cancer cells was decreased by about 20%, and the growth of A549 lung cancer cells was decreased by about 10%, compared to that of the untreated control. The growth of A375 melanoma cells was not reduced (FIG. 14).

In addition, HCT116 colorectal cancer cells and HeLa cervical cancer cells were treated with 5-AZA-CdR in the same manner as described in Experimental Example <10-1>, and the degree of apoptosis was observed under a microscope on day 5.

As a result, apoptosis was not observed in HeLa cervical cancer cells known to not respond to 5-AZA-CdR, but apoptosis induced by 5-AZA-CdR was observed in HCT116 colorectal cancer cells (FIG. 15).

The above results suggest that the degree of apoptosis is consistent with the results of the absorbance change rate of Experimental Example <10-1>, and it is possible to predict the cancer cell responsiveness to drug by measuring the dsRNA expression level.

<10-3> RT-PCR to Confirm ERV Expression

According to a recent study, 5-AZA-CdR has been reported to promote apoptosis by increasing untranslated RNA called ERV (endogenous retroviral element), the dsRNA. Thus, whether the expression of ERV (THE1B, MTL2B4, MLT1C49 and MER21C genes) was increased by 5-AZA-CdR treatment was investigated.

Total RNA was isolated from the HCT116 colorectal cancer cells treated with 5-AZA-CdR in the same manner as described in Experimental Example <10-1>, to which DNase I was treated, and then cDNA was synthesized using RevertAid reverse transcriptase (Thermo Fisher Scientific). Using the synthesized cDNA as a template, qPCR was performed with the primers in Table 1 below.

As a result, the expression levels of THE1B, MTL2B4, MLT1C49 and MER21C, the ERV, were almost unchanged on days 0 and 1, but the expression levels began to increase from day 3. In particular, the expression level of MER21C on day 5 was increased by 100 times compared to that on day 0 (FIG. 16). These results are consistent with the trends in the absorbance change rate confirmed in Experimental Example <10-1>.

TABLE 1

| Gene | Primer sequence (5'→3') Forward | Reverse |
|---|---|---|
| THE1B | TGATTTTGCAGGCTCACAG (SEQ. ID. NO: 1) | TCCTCCCAAATCTCATGTCC (SEQ. ID. NO: 2) |
| MTL2B4 | CTGCTCCCCACAGTGTCTC (SEQ. ID. NO: 3) | CAGGTTCAAACTGTTCCAG (SEQ. ID. NO: 4) |
| MLT1C49 | GGAGCTTCCTGATTGGCAGA (SEQ. ID. NO: 5) | ATGTAGGGTGGCAAGCACTG (SEQ. ID. NO: 6) |
| MER21C | TATTGCCGTACTGTGGGCTG (SEQ. ID. NO: 7) | TGGAACAGAGCCCTTCCTTG (SEQ. ID. NO: 8) |

<Experimental Example 11> Analysis of dsRNA Expression Level in Patients with Degenerative Joint Disease <11-1> Analysis of dsRNA Expression Level in Patients with Osteoarthritis, Rheumatoid Arthritis and Gout To measure the expression level of dsRNA in patients with degenerative joint disease such as osteoarthritis (OA), rheumatoid arthritis (RA) and gout, 200 μl of synovial fluid was collected from each patient, to which Trizol LS (Thermo Fisher Scientific) was treated, total and then RNA was extracted according to the manufacturer's instructions. After removing DNA by treating the total RNA with DNase I, cDNA was synthesized using a superscript cDNA synthesis kit (Thermo Fisher Scientific). Using the synthesized cDNA as a template, qPCR was performed with the primers in Table 2 below.

Even in synovial fluid, where the expression of dsRNA was expected to be low, the expression level of dsRNA in patients with degenerative joint disease was high, and dsRNAs showing the different expression levels in the synovial fluid at the same site were detected. Through this, it was confirmed that the early diagnosis of degenerative joint disease can be performed and the progression of the disease can be grasped by measuring the expression level of dsRNA (FIG. 17).

TABLE 2

| Gene | Primer sequence (5' → 3') Forward | Reverse |
|---|---|---|
| 12s rRNA | AAGGTGTAGCCCATGAGGTG (SEQ. ID. NO: 9) | GGCCCTGTTCAACTAAGCAC (SEQ. ID. NO: 10) |
| ND1 mtRNA | TCAAACTCAAACTACGCCCTG (SEQ. ID. NO: 11) | GTTGTGATAAGGGTGGAGAGG (SEQ. ID. NO: 12) |
| ND5 mtRNA | CTAGGCCTTCTTACGAGCC (SEQ. ID. NO: 13) | TTTGGGTTGAGGTGATGATG (SEQ. ID. NO: 14) |

<11-2> Analysis of dsRNA Expression Level in Osteoarthritis Patients

To measure the expression level of dsRNA in 10 patients with RA-osteoarthritis (OA), qPCR was performed with the primers in Table 3 below using the cDNA synthesized from 200 μl of synovial fluid of each patient in the same manner as described in Example <3-1> as a template.

As a result, the expression of dsRNA was high in all patients, and dsRNAs showing the different expression levels in the synovial fluid at the same site were detected (FIG. 18). These results suggest that degenerative joint disease can be diagnosed early by measuring the expression level of dsRNA.

TABLE 3

| Gene | Primer sequence (5' → 3') Forward | Reverse |
|---|---|---|
| ND1 | TCAAACTCAAACTACGCCCTG (SEQ. ID. NO: 15) | GCTGTGATAAGGGTGGAGAGG (SEQ. ID. NO: 16) |
| ND4 | CTCACACTCATTCTCAACCCC (SEQ. ID. NO: 17) | TGTTTGTCGTAGGCAGATGG (SEQ. ID. NO: 18) |
| ND5 | CTAGGCCTTCTTACGAGCCA (SEQ. ID. NO: 19) | TTTGGGTTGAGGTGATGATG (SEQ. ID. NO: 20) |
| ND6 | TGCTGTGGGTGAAAGAGTAGT (SEQ. ID. NO: 21) | CCCATAATCATAAAAGCCCC (SEQ. ID. NO: 22) |
| CYTB | CAATTATACCCTAGCCAACCCC (SEQ. ID. NO: 23) | GGATAGTAATAGGGCAAGGACG (SEQ. ID. NO: 24) |
| CO1 | GCCATAACCCAATACCAAACG (SEQ. ID. NO: 25) | TTGAGGTTGCGGTCTGTTAG (SEQ. ID. NO: 26) |
| CO2 | CTAGTCCTGTATGCCCTTTTCC (SEQ. ID. NO: 27) | GTAAAGGATGCGTAGGGATGG (SEQ. ID. NO: 28) |
| CO3 | CCTTTTACCACTCCAGCCTAG (SEQ. ID. NO: 29) | CTCCTGATGCGAGTAATACGG (SEQ. ID. NO: 30) |

<Experimental Example 12> Analysis of dsRNA Expression Level in Patients with Sjogren's Syndrome To compare the expressions of ND1 dsRNA, ND4 dsRNA, ND5 dsRNA, ND6 dsRNA, CYTB dsRNA, CO1 dsRNA, CO2 dsRNA and CO3 dsRNA present in the saliva obtained from 12 samples each of normal control (control), simple xerostomia patients (SS−) and Sjogren's syndrome (SS+) patients with xerostomia, 150 μl of saliva was collected, to which RNeasy Protect Saliva Mini Kit (Qiagen) was treated, and then total RNA was extracted according to the manufacturer's instructions. After removing DNA by treating the total RNA with DNase I, CDNA was synthesized using a superscript CDNA synthesis kit (Invitrogen Inc.). Using the synthesized cDNA as a template, qPCR was performed with the primers against various mt dsRNA elements shown in Table 3 below.

As a result, it was confirmed that the expressions of dsRNAs in Sjogren's syndrome (SS+) patients with xerostomia were all higher than those in normal people and simple xerostomia patients, which was statistically significant (FIG. 19).

What is claimed is:

1. A method for detecting double-stranded RNA (dsRNA) comprising contacting in a sample containing the dsRNA after RNase T1 and DNase I treatment on total RNAs separated from each of control and experimental group samples with a composition comprising a merocyanine compound represented by formula 1 below, said method comprising:

a) preparing a merocyanine compound represented by formula 1 below by irradiating a spiropyran compound represented by formula 2 below with ultraviolet light, wherein formula 1 is

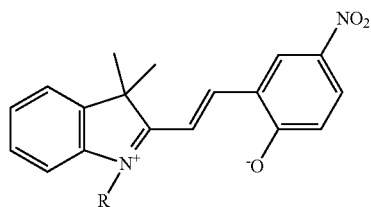

and formula 2

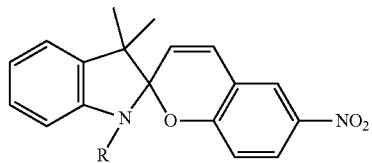

and wherein in formula 1 and formula 2, R is —CH$_2$CH$_2$CH$_2$N+(CH$_3$)$_3$ b) preparing a control sample containing the dsRNA and the sample containing the dsRNA by treating total RNA extracted from a control group and total RNA extracted from a test subject with RNase T1 respectively;

c) reacting the merocyanine compound of step a) with the control sample containing the dsRNA and the sample containing the dsRNA from step b) in a reaction solution; and d) calculating absorbance change rate at 512 nm using UV-Vis spectrometry by comparing absorbance in the control sample to absorbance in the sample containing the dsRNA from step b), wherein the absorbance change rate is proportion to dsRNA concentration.

2. The method for detecting dsRNA according to claim 1, wherein the merocyanine compound is intercalated between dsRNA nucleotides.

3. The method for detecting dsRNA according to claim 1, wherein the reaction of step c) is performed in a solution without ions.

* * * * *

SEQUENCE LISTING

<160> NUMBER OF SEQ ID NOS: 30

<210> SEQ ID NO 1
<211> LENGTH: 19
<212> TYPE: DNA
<213> ORGANISM: Artificial
<220> FEATURE:
<223> OTHER INFORMATION: THE1B F primer

<400> SEQUENCE: 1
tgattttgca ggctcacag                                           19

<210> SEQ ID NO 2
<211> LENGTH: 20
<212> TYPE: DNA
<213> ORGANISM: Artificial
<220> FEATURE:
<223> OTHER INFORMATION: THE1B R primer

<400> SEQUENCE: 2
tcctcccaaa tctcatgtcc                                          20

<210> SEQ ID NO 3
<211> LENGTH: 19
<212> TYPE: DNA
<213> ORGANISM: Artificial
<220> FEATURE:
<223> OTHER INFORMATION: MTL2B4 F primer

<400> SEQUENCE: 3
ctgctcccca cagtgtctc                                           19

<210> SEQ ID NO 4
<211> LENGTH: 19
<212> TYPE: DNA
<213> ORGANISM: Artificial
<220> FEATURE:
<223> OTHER INFORMATION: MTL2B4 R primer

<400> SEQUENCE: 4
caggttcaaa ctgttccag                                           19

<210> SEQ ID NO 5
<211> LENGTH: 20
<212> TYPE: DNA
<213> ORGANISM: Artificial
<220> FEATURE:
<223> OTHER INFORMATION: MLT1C49 F primer

<400> SEQUENCE: 5
ggagcttcct gattggcaga                                          20

<210> SEQ ID NO 6
<211> LENGTH: 20
<212> TYPE: DNA
<213> ORGANISM: Artificial
<220> FEATURE:

<223> OTHER INFORMATION: MLT1C49 R primer

<400> SEQUENCE: 6
atgtagggtg gcaagcactg                                         20

<210> SEQ ID NO 7
<211> LENGTH: 20
<212> TYPE: DNA
<213> ORGANISM: Artificial
<220> FEATURE:
<223> OTHER INFORMATION: MER21C F primer

<400> SEQUENCE: 7
tattgccgta ctgtgggctg                                         20

<210> SEQ ID NO 8
<211> LENGTH: 20
<212> TYPE: DNA
<213> ORGANISM: Artificial
<220> FEATURE:
<223> OTHER INFORMATION: MER21C R primer

<400> SEQUENCE: 8
tggaacagag cccttccttg                                         20

<210> SEQ ID NO 9
<211> LENGTH: 20
<212> TYPE: DNA
<213> ORGANISM: Artificial
<220> FEATURE:
<223> OTHER INFORMATION: 12s rRNA F primer

<400> SEQUENCE: 9
aaggtgtagc ccatgaggtg                                         20

<210> SEQ ID NO 10
<211> LENGTH: 20
<212> TYPE: DNA
<213> ORGANISM: Artificial
<220> FEATURE:
<223> OTHER INFORMATION: 12s rRNA R primer

<400> SEQUENCE: 10
ggccctgttc aactaagcac                                         20

<210> SEQ ID NO 11
<211> LENGTH: 21
<212> TYPE: DNA
<213> ORGANISM: Artificial
<220> FEATURE:
<223> OTHER INFORMATION: ND1 mtRNA F primer

<400> SEQUENCE: 11
tcaaactcaa actacgccct g                                       21

<210> SEQ ID NO 12
<211> LENGTH: 21
<212> TYPE: DNA
<213> ORGANISM: Artificial
<220> FEATURE:
<223> OTHER INFORMATION: ND1 mtRNA R primer

<400> SEQUENCE: 12
gttgtgataa gggtggagag g                                       21

```
<210> SEQ ID NO 13
<211> LENGTH: 19
<212> TYPE: DNA
<213> ORGANISM: Artificial
<220> FEATURE:
<223> OTHER INFORMATION: ND5 mtRNA F primer

<400> SEQUENCE: 13
ctaggccttc ttacgagcc                                                19

<210> SEQ ID NO 14
<211> LENGTH: 20
<212> TYPE: DNA
<213> ORGANISM: Artificial
<220> FEATURE:
<223> OTHER INFORMATION: ND5 mtRNA R primer

<400> SEQUENCE: 14
tttgggttga ggtgatgatg                                               20

<210> SEQ ID NO 15
<211> LENGTH: 21
<212> TYPE: DNA
<213> ORGANISM: Artificial
<220> FEATURE:
<223> OTHER INFORMATION: ND1 F primer

<400> SEQUENCE: 15
tcaaactcaa actacgccct g                                             21

<210> SEQ ID NO 16
<211> LENGTH: 21
<212> TYPE: DNA
<213> ORGANISM: Artificial
<220> FEATURE:
<223> OTHER INFORMATION: ND1 R primer

<400> SEQUENCE: 16
gctgtgataa gggtggagag g                                             21

<210> SEQ ID NO 17
<211> LENGTH: 21
<212> TYPE: DNA
<213> ORGANISM: Artificial
<220> FEATURE:
<223> OTHER INFORMATION: ND4 F primer

<400> SEQUENCE: 17
ctcacactca ttctcaaccc c                                             21

<210> SEQ ID NO 18
<211> LENGTH: 20
<212> TYPE: DNA
<213> ORGANISM: Artificial
<220> FEATURE:
<223> OTHER INFORMATION: ND4 R primer

<400> SEQUENCE: 18
tgtttgtcgt aggcagatgg                                               20

<210> SEQ ID NO 19
<211> LENGTH: 20
<212> TYPE: DNA
<213> ORGANISM: Artificial
<220> FEATURE:
<223> OTHER INFORMATION: ND5 F primer
```

<400> SEQUENCE: 19
ctaggccttc ttacgagcca                                              20

<210> SEQ ID NO 20
<211> LENGTH: 20
<212> TYPE: DNA
<213> ORGANISM: Artificial
<220> FEATURE:
<223> OTHER INFORMATION: ND5 R primer

<400> SEQUENCE: 20
tttgggttga ggtgatgatg                                              20

<210> SEQ ID NO 21
<211> LENGTH: 21
<212> TYPE: DNA
<213> ORGANISM: Artificial
<220> FEATURE:
<223> OTHER INFORMATION: ND6 F primer

<400> SEQUENCE: 21
tgctgtgggt gaaagagtag t                                            21

<210> SEQ ID NO 22
<211> LENGTH: 20
<212> TYPE: DNA
<213> ORGANISM: Artificial
<220> FEATURE:
<223> OTHER INFORMATION: ND6 R primer

<400> SEQUENCE: 22
cccataatca taaaagcccc                                              20

<210> SEQ ID NO 23
<211> LENGTH: 22
<212> TYPE: DNA
<213> ORGANISM: Artificial
<220> FEATURE:
<223> OTHER INFORMATION: CYTB F primer

<400> SEQUENCE: 23
caattatacc ctagccaacc cc                                           22

<210> SEQ ID NO 24
<211> LENGTH: 22
<212> TYPE: DNA
<213> ORGANISM: Artificial
<220> FEATURE:
<223> OTHER INFORMATION: CYTB R primer

<400> SEQUENCE: 24
ggatagtaat agggcaagga cg                                           22

<210> SEQ ID NO 25
<211> LENGTH: 21
<212> TYPE: DNA
<213> ORGANISM: Artificial
<220> FEATURE:
<223> OTHER INFORMATION: CO1 F primer

<400> SEQUENCE: 25
gccataaccc aataccaaac g                                            21

<210> SEQ ID NO 26
<211> LENGTH: 20

```
<212> TYPE: DNA
<213> ORGANISM: Artificial
<220> FEATURE:
<223> OTHER INFORMATION: CO1 R primer

<400> SEQUENCE: 26
ttgaggttgc ggtctgttag                                            20

<210> SEQ ID NO 27
<211> LENGTH: 22
<212> TYPE: DNA
<213> ORGANISM: Artificial
<220> FEATURE:
<223> OTHER INFORMATION: CO2 F primer

<400> SEQUENCE: 27
ctagtcctgt atgccctttt cc                                         22

<210> SEQ ID NO 28
<211> LENGTH: 21
<212> TYPE: DNA
<213> ORGANISM: Artificial
<220> FEATURE:
<223> OTHER INFORMATION: CO2 R primer

<400> SEQUENCE: 28
gtaaaggatg cgtagggatg g                                          21

<210> SEQ ID NO 29
<211> LENGTH: 21
<212> TYPE: DNA
<213> ORGANISM: Artificial
<220> FEATURE:
<223> OTHER INFORMATION: CO3 F primer

<400> SEQUENCE: 29
ccttttacca ctccagccta g                                          21

<210> SEQ ID NO 30
<211> LENGTH: 21
<212> TYPE: DNA
<213> ORGANISM: Artificial
<220> FEATURE:
<223> OTHER INFORMATION: CO3 R primer

<400> SEQUENCE: 30
ctcctgatgc gagtaatacg g                                          21
```